United States Patent [19]
Thomas et al.

[11] Patent Number: 6,140,309
[45] Date of Patent: Oct. 31, 2000

[54] VASOACTIVE EFFECTS AND FREE RADICAL GENERATION BY β-AMYLOID PEPTIDES

[75] Inventors: Thomas N. Thomas, Palm Harbor; Michael Mullan, Tampa Palms, both of Fla.

[73] Assignee: University of South Florida, Tampa, Fla.

[21] Appl. No.: 08/615,593

[22] Filed: Mar. 12, 1996

[51] Int. Cl.[7] ................................................ A01N 43/04
[52] U.S. Cl. ........................... 514/43; 424/94.4; 424/718
[58] Field of Search ............................. 514/43; 424/718, 424/94.4

[56] References Cited

U.S. PATENT DOCUMENTS

| | | | |
|---|---|---|---|
| 4,439,196 | 3/1984 | Higuchi | 604/890 |
| 4,447,224 | 5/1984 | DeCant, Jr. et al. | 604/67 |
| 4,447,233 | 5/1984 | Mayfield | 604/152 |
| 4,475,196 | 10/1984 | La Zor | 371/29 |
| 4,486,194 | 12/1984 | Ferrara | 604/897 |
| 4,487,603 | 12/1984 | Harris | 604/152 |
| 4,736,866 | 4/1988 | Leder et al. | 800/1 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,221,778 | 6/1993 | Byrne et al. | 800/2 |
| 5,288,846 | 2/1994 | Quertermous et al. | 435/172.3 |
| 5,298,422 | 3/1994 | Schwartz et al. | 435/320.1 |
| 5,347,075 | 9/1994 | Sorge | 800/2 |
| 5,360,735 | 11/1994 | Weinshank et al. | 435/240.2 |
| 5,387,742 | 2/1995 | Cordell | 800/2 |

FOREIGN PATENT DOCUMENTS

| | | |
|---|---|---|
| 9314200 | of 0000 | WIPO . |
| 9406908 | of 0000 | WIPO . |
| 9423049 | of 0000 | WIPO . |
| 9428123 | of 0000 | WIPO . |

OTHER PUBLICATIONS

Beckman et al., "ALS, SOD and peroxynitrite" *Nature*, 364:584 (1993).

Bennett et al., "Evidence That the APOE Locus Influences Rate of Disease Progression in late Onset Familial Alzheimer's Disease . . . " *Amer. J. of Medical Genetics (Neuropsychiatric Genetics)*, 60:1–6 (1995).

Betz et al., *Basic Neurochem.* Molecular Cell, (Raven Press Ltd., NY) 5th Ed., pp. 681–699 (1994).

Blennow et al., "White–matter lesions on CT in Alzheimer patients: relations to clinical . . . ", *Acta Neurologica Scandinavica* 83 (3):187–93.

Buee et al., "Pathological alterations of the cerebral microvasculature in Alzheimer's disease and related dementing disorders" *Acta Neuropathol* 87:469–480 (1994).

Bulkley G.B. Free Radicals and other reactive oxygen metabolites: Clinical relevance and the therapeutic efficacy of antioxidant therapy *Surgery* vol. 113, No. 5, pp. 479–484 (1993).

Burke et al., "Blood pressure regulation in Alzheimer'disease" *Journal of the Autonomic Nervous System* 48 (1) pp. 65–71 (1994).

Burke and Olson, "Preparation of Clone Libraries in Yeast Artificial–Chromosome Vectors" *Methods in Enzymology*, vol. 194, "Guide to Yeast Genetics and Molecular Biology" Chap. 17, pp. 251–270 (1991).

Byung Pal Yu, "Cellular Defenses against damage from reactive oxygen species" *Physiological Reviews* vol. 74, No. 1, pp. 139–162 (1994).

Capecchi, "Altering the Genome by Homologous Recombinations" *Science* vol. 244 pp. 1288–1292 (1989).

Corder et al., "Gene Dose of Apolipoprotein E type 4 Allele and the Risk of Alzheimer's Disease in Late Onset Families" *Science* vol. 261, pp. 921–923 (1993).

Davies et al., "Targeted alterations in yeast artificial chromosomes for inter–species gene transfer" *Nucleic Acids Research*, vol. 20, No. 11, pp. 2693–2698 (1992).

Davignon et al., "Apolipoprotein E Polymorphism and Atherosclerosis" *Arterlosclerosis* 8:1–21, (1988).

Dickinson et al., "High frequency gene targeting using insertional vectors" *Human Molecular Genetics*, vol. 2, No. 8 pp. 1299–1302 (1993).

Elmstahl et al., "Autonomic cardiovascular reponses to tilting in patients with Alzheimer's disease and in healthy elderly women" *Age and Aging*. 21 4): 301–7 (1992).

Etcheberrigaray et al., Soluble β–Amyloid Induction of Alzheimer's Phenotype for Human Fibroblast $K^+$ Channels *Science* 264:276–279 (1994).

Furchgott and Zawadzki, "The Obligatory role of endothelial cells in the relaxation of arterial smooth muscle by acetylcholine" *Nature*, vol. 288:373–376 (1980).

Furchgott et al., *Jap. J. Pharmacol.* 58: Suppl. 2, pp. 185–191 (1992).

Gilligan et al., "Acute Vascular Effects of Estrogen in Postmenopausal women" *Circulation* vol. 90, No. 2, pp. 786–791 (1994).

Gimbrone et al., "Vascular Endothelium: An Integrator of Pathophysiological Stimuli in Atherogenesis" *Ann. New York Acad. of Science* 148:122–131 (1995).

Glenner and Wong, "Alzheimer's Disease: Initial report of the purification and characterization of a novel cerebrovascular . . . " *Biochem. Biophys. Res. Commun.*, vol. 120, No. 3, pp. 855–890 (1984).

Greenberg et al., "Apolipoprotein E ∈4 and Cerebral Hemorrhage Associated with Amyloid Angiopathy" *Annals of Neurology*, vol. 38,. No. 2, pp. 254–259 (1995).

Edward D. Hall, "Lipid Antioxidants in Acute Central Nervous System Injury" *Annals of Emergency Medicine*, 22:1022–1027 (1993).

(List continued on next page.)

*Primary Examiner*—Dwayne C. Jones
*Attorney, Agent, or Firm*—Kohn & Associates

[57] ABSTRACT

A method is disclosed for treating and preventing diseases, wherein at least one of the causes of the disease is β-amyloid peptide induced change in free radical production resulting in vascular endothelial dysfunction and vasoactivity, by antagonizing vascular free radicals in excess of functional equilibrium.

9 Claims, 14 Drawing Sheets

OTHER PUBLICATIONS

Harmon, "Free Radical theory of Aging: A hypothesis on pathogenesis of senile dementia of the alzheimer's type" *Age*, vol. 16, pp. 23–30 (1993).

Huxley et al., "The human HPRT Gene on a Yeast Artificial Chromosome Is Functional When Transferred to Mouse Cells by Cell Fusion", *Genomics*, 9:742–750 (1991).

Hyman et al., "Nitric Oxide Synthase–Containing Neurons in the Hippocarnpal Formation in Alzheimer's Disease" *Ann. Neurol.* 32:818–820 (1992).

Jakobovits et al., "Germ–line transmission and expression of a human–derived yeast artificial chromosome", *Nature*, vol. 362, pp. 255–261 (1993).

Katusic and Vanhoutte, "Superoxide anion is an endothelium–derived contracting factor" *Am. J. Physiol.* 257:H33–7 (1989).

Kontos et al., "Oxygen radicals mediate the cerebral arteriolar dilation from arachidonate and bradykinin in cats" *Circ. Res.* 55:295–303 (1984).

Kureja et al., "PGH Synthase and Lipoxygenase Generate Superoxide in the presence of NADH or NADPH" *Circulation Research*, vol. 59, No. 6 pp. 612–619 (1986).

Lamb et al., "Introduction and expression of the 400 kilobase precursor amyloid protein gene in transgenic mice" *Nature Genetics*, vol. 5, pp. 22–29 (1993).

Lipton et al., "A redox–based mechanism for the neuroprotective and neurodestructive effects of nitric oxide and related nitroso–compounds" *Nature*, vol. 364, pp. 626–632 (1993).

Mandybur T.I., "The Incidence of cerebral amyloid angiopathy in alzheimer's disease" *Neurology*, 25:120–126 (1975).

Marshall et al., "Independent blockade of cerebral vasodilation from acetylcholine and nitric oxide" *Am. J. Physiol.* 255:H847–54 (1988).

Mattson et al., "β–Amyloid precursor protein metabolites and loss of neuronal $Ca^{2+}$ hmeostasis in alzheimer's disease" *TINS* 16:409–414 (1993).

Matt–Schieman M. et al., "Hereditary cerebral hemorrhage with amyloidisis (Dutch): a model for congrophilic plaque . . . " *Acta Neuropathologica* 88(4):371–8 (1994).

Moncada et al., "Endothelium–derived relaxing factor: identification as nitric oxide and role in the control of vascular tone and platelet function" *Biochem. Pharmacol.* 37:2494–2501 (1988).

Nathan et al., "Differential Effects of Apolipoproteins E3 and E4 on neuronal growth in vitro" *Science*, vol. 264:850–852 (1994).

Olanow, C.W., "A radical hypothesis for neurodegeneration", *TINS*, 16:439–444 (1993).

Pardridge, "Blood–brain barrier and new approaches to brain drug delivery", *The Western Journal of Medicine* 156(3) pp. 281–286 (1992).

Pardridge, "Recent Development in Peptide Drug Delivery to the brain" *Pharmacology & toxicology*, 71(1) pp. 3–10 (1992).

Pardridge et al., *Proc. Natl. Acad. Sci. USA* 90(7) 2618–2622 (1993).

Pomara et al., "Pretreatment postural blood pressure drop as a possible predictor of response to the cholinesterease inhibitor . . . " *Psychopharmacology Bulletin* 27 (3) pp. 301–307 (1991).

Pou et al., "Generation of superoxide by purified brain nitric oxide synthase" *Journal of Biological Chemistry*, vol. 267, No. 34, pp. 24173–24176 (1992).

Price et al., "Toxicity of synthetic Aβ peptides and modeling of alzheimer's disease" *Neurobiology of Aging*, vol. 13, pp. 623–625 (1992).

Rosenblum, "Effects of free radical generation on mouse pial arterioles: probable role of hydroxyl radicals" *Am. J. Physiol.*, 245:H 139–42 (1983).

Rosenblum, "Hydroxyl radical mediates the Endothelium–dependent Relaxation Produced by Bradykinin in Mouse Cerebral Arterioles" *Circulation Research*, vol. 61, No. 4 pp. 601–603 (1987).

Rossor, et al., "Alzheimer's disease families with amyloid precursor protein mutations" *Annals of the New York Academy of Sciences*, 24:695:198–202 (1993).

Rothstein, Targeting, disruption, replacement, and allele rescue: integrative DNA transformation in yeast, *Methods in Enzymology*, vol. 194, pp. 281–301 (1991).

Saunders, a. et al., "Association of Apolipoprotein E allele with late onset familial and sporadic alzheimer's disease" *Neurology* 43: (1993).

Savita, Prashar et al., "Antoxident enzymens in RBC as a biological index of age related macular degeneration", *Acta Opthalmologica* 71:214–218 (1993).

Schedl et al., "A yeast artificial chromosome covering the tyrosinase gene confers copy number–dependent expression in transgenic mice" *Nature*, vol. 362, pp. 258–261 (1993).

Schneider et al., "Do blood pressure and age predict response to tacrine (THA) in alzheimer's disease? A preliminary report" *Psychopharmacology Bulletin*, vol. 27, No. 3, pp. 309–314 (1991).

Sneddon and Vane, "Endothelium–derived relaxing factor reduces platelet adhesion to bovine endothelial cells" *Proc. Natl. Acad. Sci. USA*, 85:2800–2804 (1988).

Strauss et al., "Germ line transmission of a yeast artificial chromosome spanning the murine $\alpha_1$ (I) Collagen Locus", *Science* vol. 259, pp. 1904–1907 (1993).

Strittmatter, D. et al., "Apolipoprotein E: High–avidity binding to β–amyloid and increased frequency of type 4 allele in late–onset familial alzheimer disease", *Proc. Natl. Acad. Sci. U.S.A.* 90: (1993a).

Strittmatter, et al. "Binding of human apolipoprotein E to synthetic amyloid β peptide: Isoform–specific effects and . . . " *Proc. Natl. Acad. Sci. U.S.A.* vol. 90, pp. 8098–8102 (1993).

Thomas et al., "β–Amyloid–mediated vasoactivity and vascular endothelial damage" *Nature*, vol. 380, pp. 168–171 (1996).

Tomimoto et al., "Temporal profiles of acccumulation of amyloid β/A4 protein precursor in the gerbil after graded ischemic stress" *J. of Cerebral blood Flow and Metabolism*, 14:(4):565–573 (1994).

Vinters H.V. "Progress Review Cerebral Amyloid Angiopathy a critical review", *Stroke*, vol. 18, No. 2, pp. 311–324 (1987).

Waldemar et al,. "White matter magnetic resonance hyperintensities in dementia of the alzheimer type: morphological and regional . . . " *J. of Neurology, Neurosurgery, and Psy.*, 57 (12): 1458–1465 (1994).

Wang, S. et al., "Cardiovascular autonomic functions in alzherimer's disease", *Age & aging*, 23(5):400–4 (1994).

Wei et al, "Superoxide generation and reversal of acetylcholine–induced cerebral arteriolar dilation after acute hypertension" *Circulation Research*, vol. 57, No. 5, pp. 781–787 (1985).

Yanker et al., "Neurotrophic and neurotoxic effects of amyloid β protein: reversal by tachykinin neuropeptides" *Science*, vol. 250, pp. 279–282 (1990).

Zubenko et al., "association of the apolipoprotein E ε 4 allele with clinical subtypes of autopsy–confirmed alzheimer's . . . " *American J. of Medical Genetics*, 15: 54(3):199–205 (1994).

Dawson et al., "Contemporary Issues in Toxicology: Excitotoxins, Aging, and Enviromental Neurotoxins: Implications for Understanding Human . . . " *Toxiclogy and Applied Pharmacology* 134, 1–17 (1995).

Inoue et al., "Inhibition of oxygne toxicity by targeting superoxide dismutase to endothelial cell surface" *FEBS* vol. 269, No. 1, pp. 89–92 (1990).

Oury et al., "Cold–induced Brain Edema in Mice" *The Journal of Biological Chemistry* oo, 15394–15398 (1993).

Winblad, Apolipoprotein e Epsilon–4–Allele, Skin Vessel Reactivity and Vascular Risk Factors in Alzheimers Disease Archives of Genontology & Geriatrics 22(3)L2230232 (1996), abstract.

Subramaniam, R. et al., "Beta–Amyloid (32–35) toxicity to biomolecules: implications to Alzheimer's disease.", Alzheimer's Res., 1(3), pp. 141–144, 1995, (see abstract).

Butterfield, D. et al., "Direct evidence of oxidative injury produced by the Alzheimer's beta–amyloid peptide (1–40) in cultured hippocampal neurons.", Exp. Neurol., 131(2), pp. 193–202, 1995, (see abstract).

Behl, C. et al., "Hydrogen peroxide mediates amyloid beta protein toxicity.", Cell 77(6), pp. 817–827, 1994, (see abstract).

Byung Pal Yu, "Cellular Defenses against damage from reactive oxygen species", Physiological Reviews, vol. 74, No. 1, pp. 139–162, 1994.

Glenner, G. G. et al., "Alzheimer's disease and Down's syndrome: sharing of a unique cerebrovascular amyloid fibril protein", Biochemical and Biophysical Research Communications, vol. 122, No. 3, pp. 1131–1135, 1984.

Patel, "Pharmacotherapy of Cognitvie Impairment in Alzheimer's Disease: A Review", Journal of Geriatic Psychiatry and Neurology, vol. 8, pp. 81–95, Apr. 1995.

De Jonge et al., Nimodipine: Cognition, Aging, and Degeneration. *Clin. Neuropharmacol.*, (1993) 16/Suppl. 1 (S25–S30).

1 - CONTROL
2 - + Aβ PROTEIN
3 - ACTIVE SOD + Aβ PROTEIN
4 - ALBUMIN + Aβ PROTEIN
5 - HEAT INACTIVATED SOD + Aβ PROTEIN
6 - H₂O₂ INACIVATED SOD + Aβ PROTEIN

VASOACTIVE EFFECTS AND FREE RADICAL GENERATION BY β-AMYLOID PEPTIDES

TECHNICAL FIELD

The present invention relates to methods for treating and preventing diseases caused, at least in part, by β-amyloid peptide induced free radical production in vertebrate animals, including humans. More specifically, such methods for identifying and preventing endothelial dysfunction and/or destruction and vasoactivity have utility in the fields of diagnostics and therapeutics and in the further understanding of the physiological and pharmacological relationship between β-amyloid peptides and vasoactivity and between β-amyloid peptides and free oxygen radicals.

BACKGROUND OF THE INVENTION

The protein β-amyloid (A4, Aβ, $A\beta_{1-39-42}$) has long been central to the neuropathology of Alzheimer's disease [Glenner and Wong, 1984]. However, its role in the disease process of Alzheimer's disease and other diseases, as well as its mechanism of action, remains in dispute.

It is undisputed that β-amyloid protein is a major component of the neuritic plaques which, along with the neurofibrillary tangles, provide the neuropathological diagnostic markers for Alzheimer's disease [Mattson, 1995; Vantner et al., 1991]. It is deposited around cerebral blood vessels in Alzheimer's disease [Scholz, 1938; Mandybur, 1975; Vinters, 1987].

The sequence for β-amyloid is known [Glenner et al. 1984].

Emphasis has been on Alzheimer's being a neurological disease, not a vascular disease.

It has been suggested in Alzheimer's disease pathogenesis that β-amyloid has putative neurotoxic properties. However, there has been no consistent detection of such neurotoxic effects and there are conflicting reports [Price et al. 1992].

Referring to Teller et al. (1996), deposits of insoluble fibrils of amyloid β-peptide (Aβ) in the brain is a prominent neuropathological feature of all forms of Alzheimer's Disease (AD) regardless of the genetic predisposition of the subject. In addition to the deposition of Aβ in senile plaques and neurofibrillary tangles, vascular amyloid deposition resulting in cerebral amyloid angiopathy is a hallmark of AD and related disorders such as Down's Syndrome. The abnormal accumulation of Aβ is due to either over expression or altered processing of amyloid precursor protein (APP), a transmembrane glycoprotein. Soluble Aβ containing forty amino acids ($A\beta_{40}$) and to a lesser degree the peptide with forty-two amino acids ($A\beta_{42}$) forms the core of the amyloid deposits. The APP gene is highly conserved across different species and APPmRNA has been detected in all tissues, suggesting a normal physiologic role for Aβ. The cellular origin of Aβ deposited in the brain or cerebral blood vessels in AD or its precise role in the neurodegenerative process has not been established.

Another prominent etiologic theory of Alzheimer's disease recognizes and attempts to make consistent the etiology of the disease with the free radical theory of aging [Harman, 1986]. Free radicals are known to be neurotoxic and have been implicated with Alzheimer's disease pathophysiology. However, there has been no direct relationship shown or even suggested between β-amyloid and free radical formation. Again, these theories revolve around the concept of a neurological disease and not any contribution of a vascular disease.

The generation of toxic oxygen radicals by Aβ has been investigated as a factor contributing to the neurotoxicity of Aβ and the observation that Apolipoprotein ε4 allele is a risk factor for both vascular diseases and AD has renewed interest in the vascular abnormalities in AD. Applicants have discovered a novel and direct action of AD on blood vessels [Thomas et al. (1996) in press]. Applicants have demonstrated that Aβ interacts with endothelial cells on blood vessels causing an imbalance in the ratio of nitric oxide to other free radicals, notably superoxide, with attendant endothelial dysfunction and/or damage and alterations in vascular tone. Free radicals are known to mediate normal physiology of vasculature and modest disruption of this system would result in dysfunction but not necessarily damage. In normal situations, levels of antioxidants may be adequate to provide protection.

The present invention recognizes, for the first time, an association between β-amyloid peptide-induced free radical excess and resultant small vessel diseases including Alzheimer's disease. Although large blood vessel disease with dementia is considered distinct from Alzheimer's disease, several studies note similar pathological changes in the microvasculature in Alzheimer's disease and related neurodegenerative disorders [Buee et al., 1994].

The present invention recognizes the vasoactive effect of β-amyloid peptides, its relationship to the production of free radicals, and, therefore, recognizes a direct association between β-amyloid and vascular function and vascular degenerative diseases. The discovery further suggests the possibility that β-amyloid activity at the endothelial cell surface can precipitate damage to neurons and result in Alzheimer pathology. Based on these discoveries, therapeutic and diagnostic protocols have been developed to utilize these properties.

SUMMARY OF THE INVENTION AND ADVANTAGES

In accordance with the present invention, there is provided a method for preventing diseases, wherein at least one of the causes of the disease includes β-amyloid peptide-induced change in free radical production resulting in vascular endothelial dysfunction and vasoactivity, by antagonizing vascular free radicals in excess of functional equilibrium.

The present invention further provides a method of producing a vasoactive effect by exposing a vessel having intact endothelium to a β-amyloid peptide.

The present invention further provides a method of inhibiting the vasoactive effects of β-amyloid peptides by exposing a vessel to a modifier of superoxide formation or destruction prior to exposure of the vessel to a β-amyloid peptide.

Further, the present invention provides a method of inhibiting physiological effects of β-amyloid peptides on a tissue by exposing the tissue to a member of the group including β-amyloid antagonists, anti-oxidants, free radical scavengers, and nitric oxide compounds.

BRIEF DESCRIPTION OF THE FIGURES

Other advantages of the present invention will be readily appreciated as the same becomes better understood by reference to the following detailed description when considered in connection with the accompanying drawings wherein.

Figure 15:
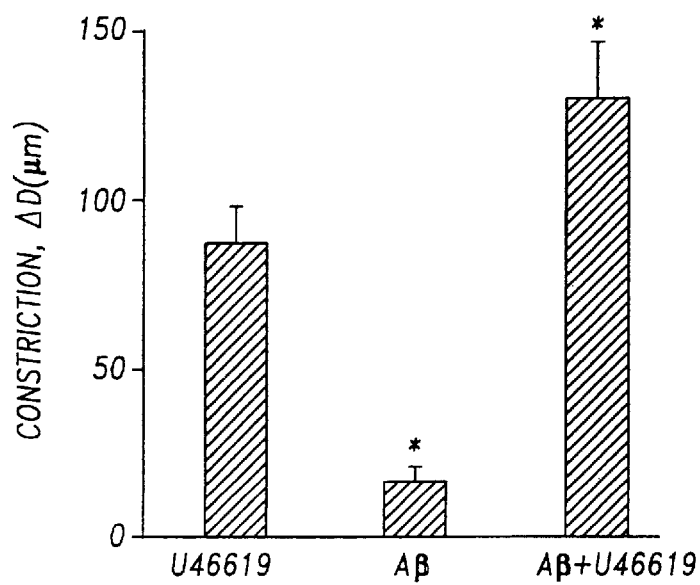
Figure 14A:
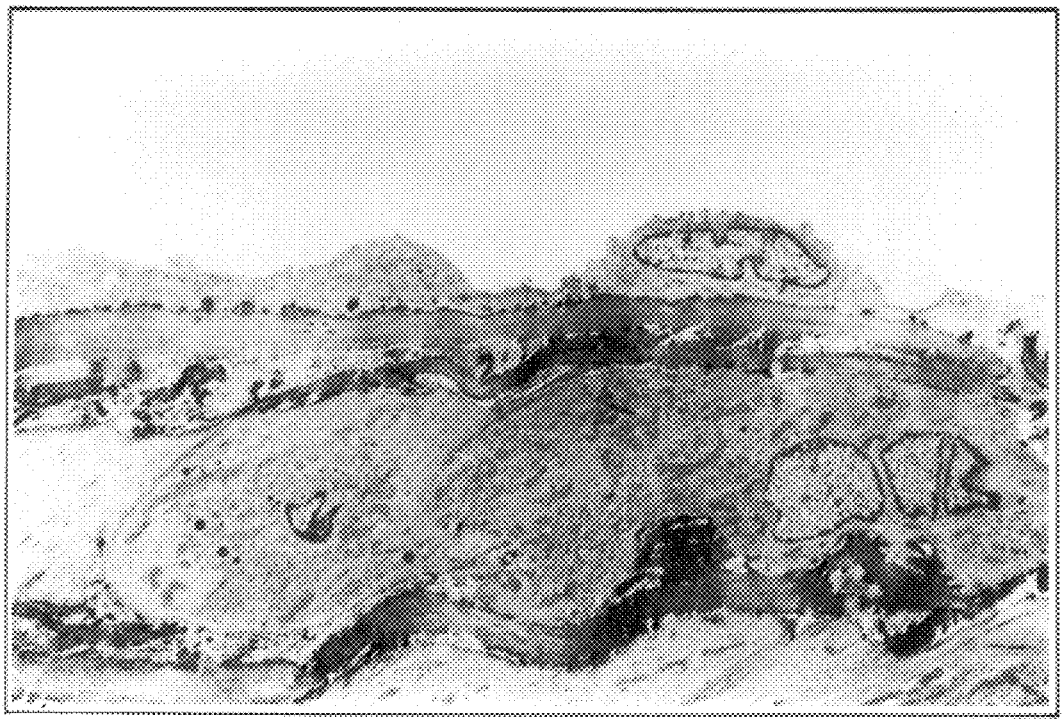
FIGS. 14A–F are electron micrographs showing the endothelial cell layers in aortic rings, (A) Control aorta at a magnification of 2,400, three normal endothelial cells are visible closely adhering to the intimal elastic lamina lining the lumen, one sectioned showing the nucleus while two missed the nuclear area in this section.
Figure 14B:
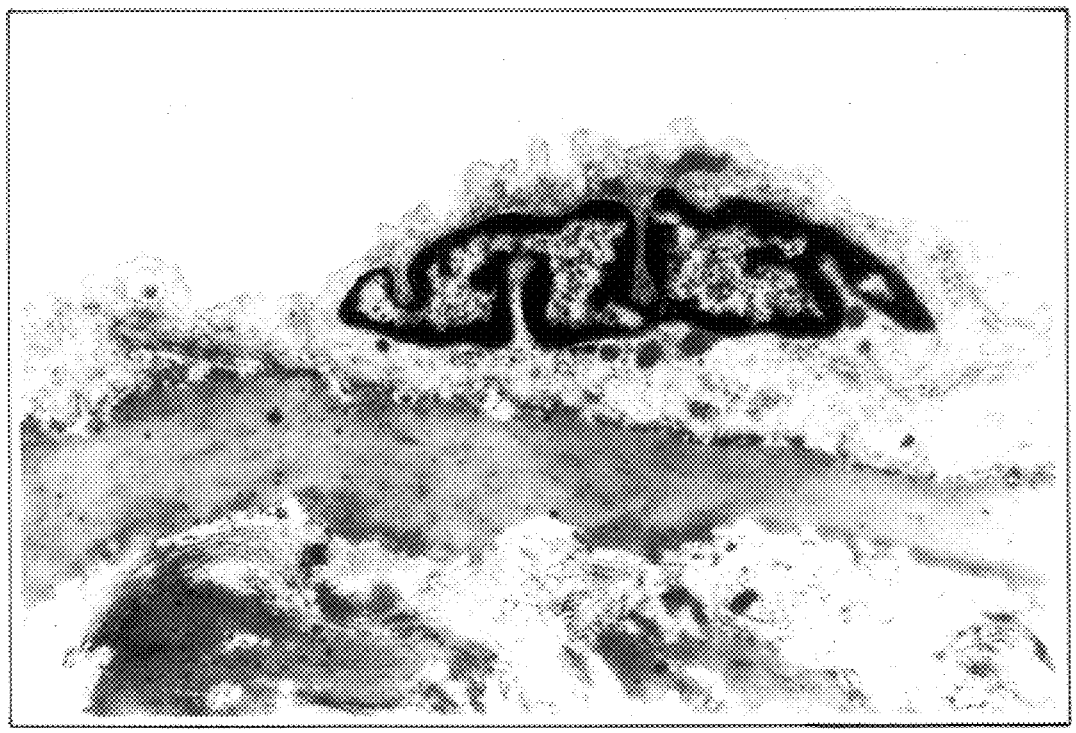
Figure 14C:
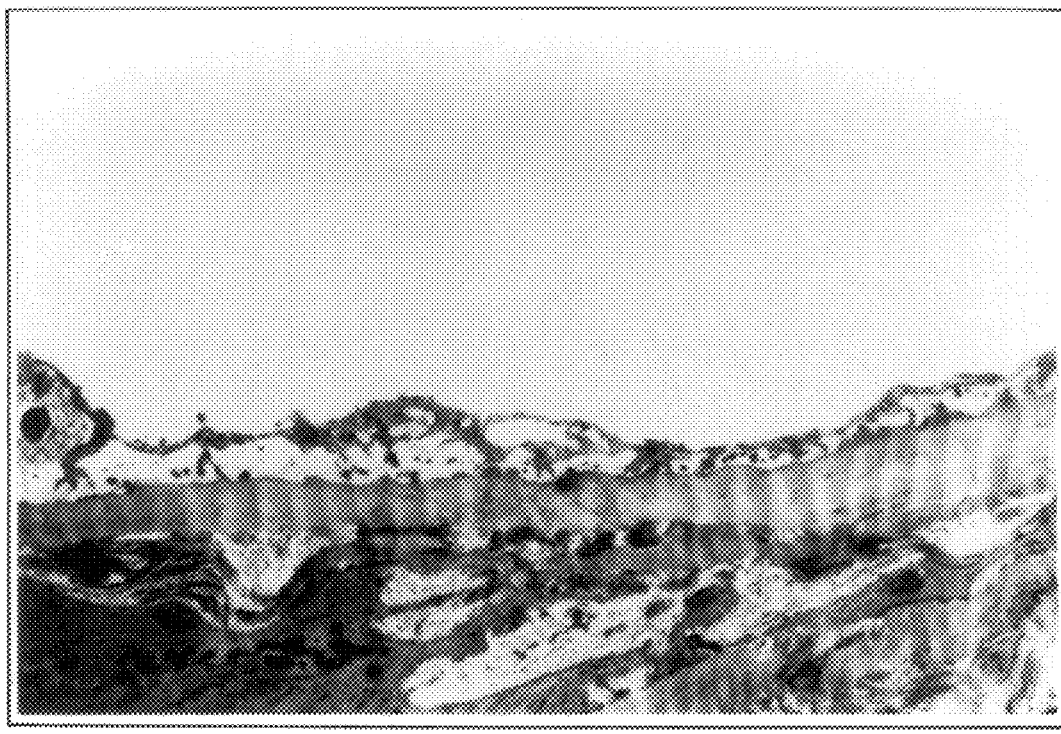
Figure 14D:
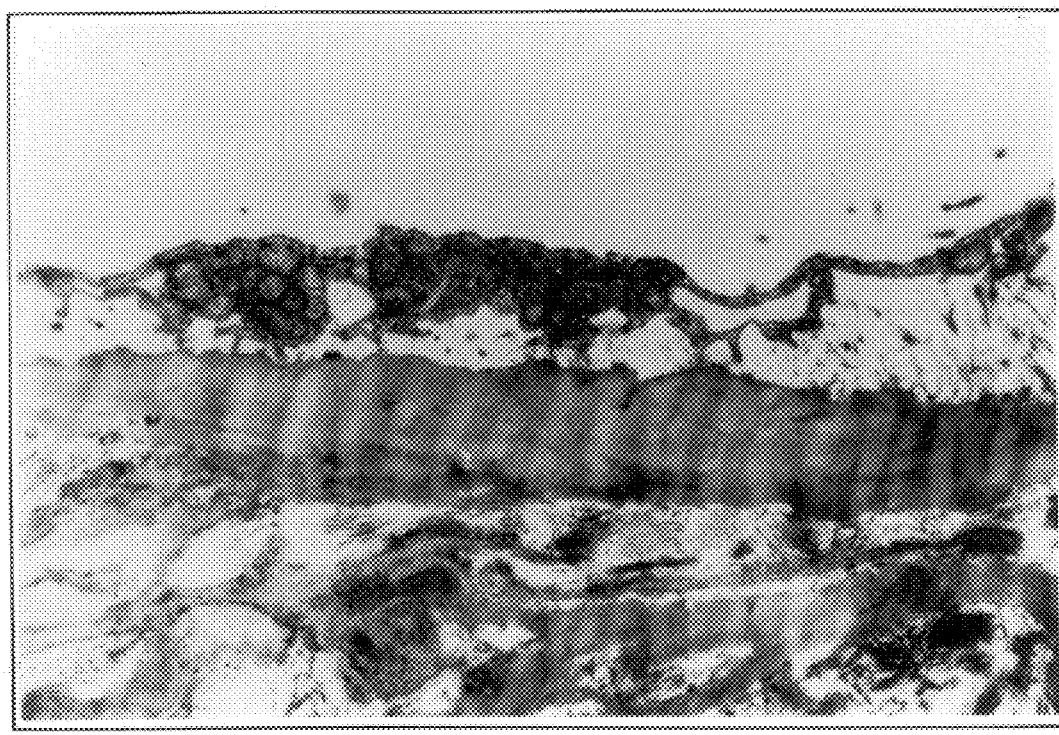
Figure 14E:
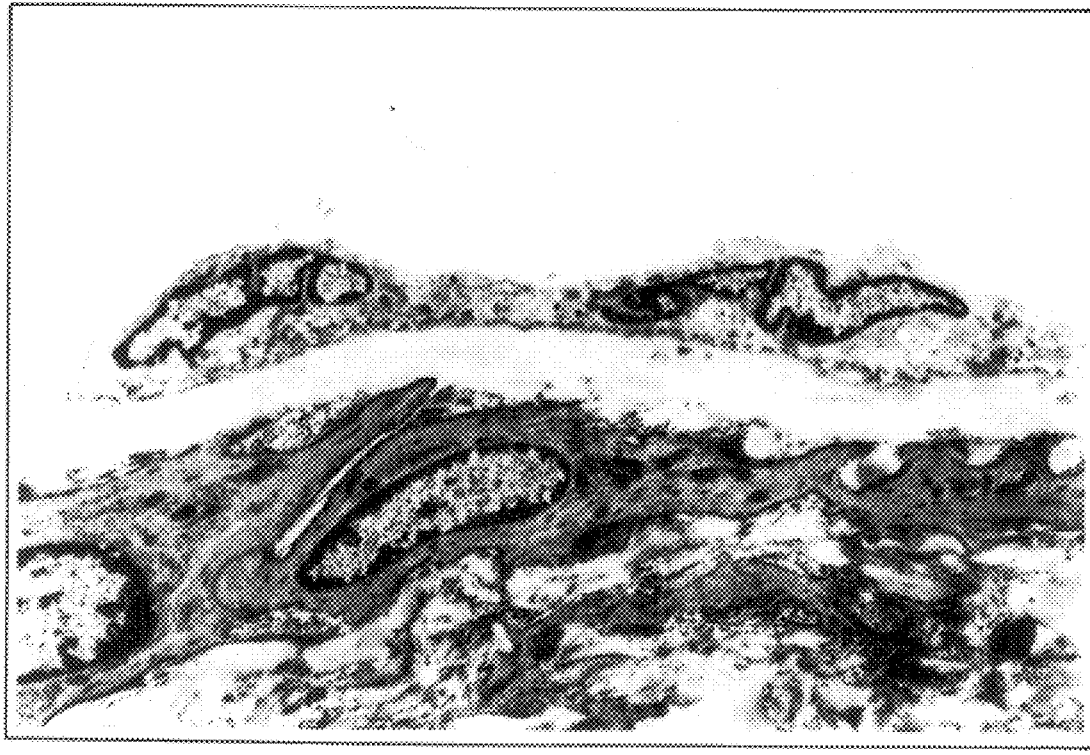
Figure 14F:
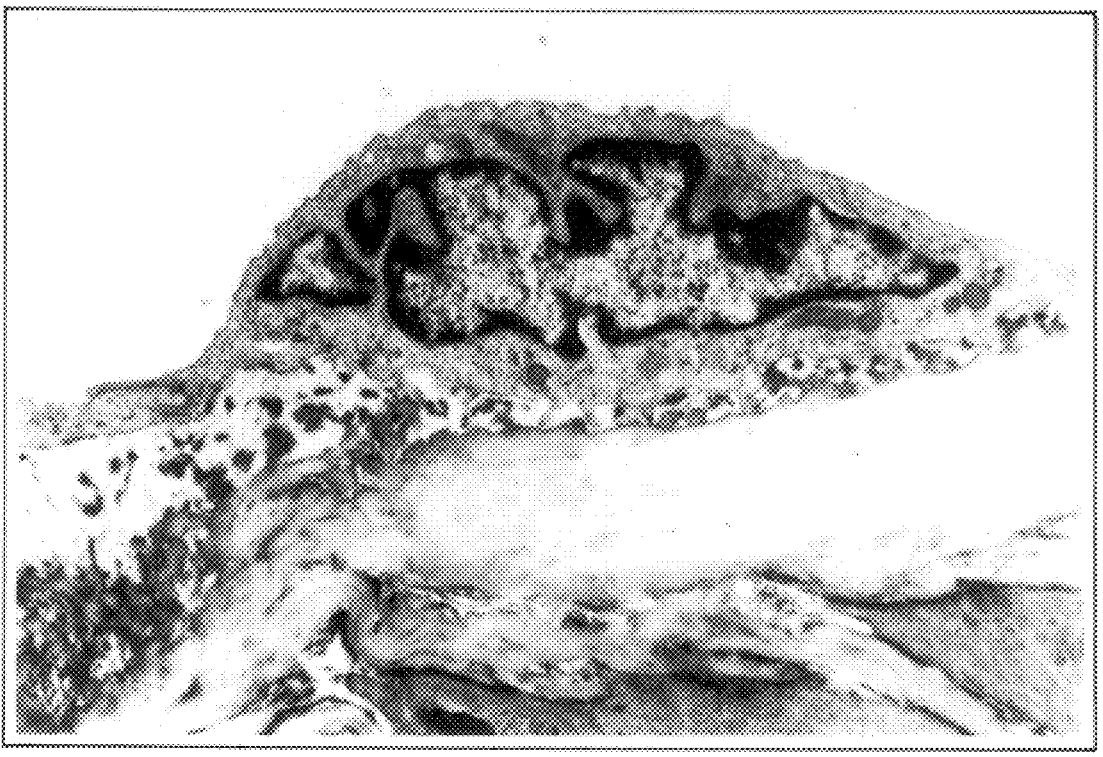
Figure 16:
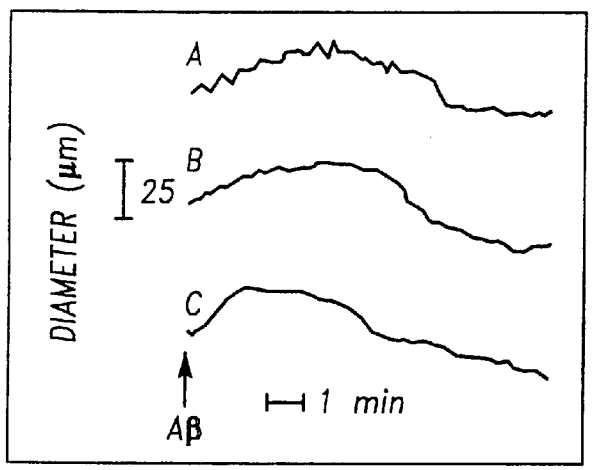
Figure 17:
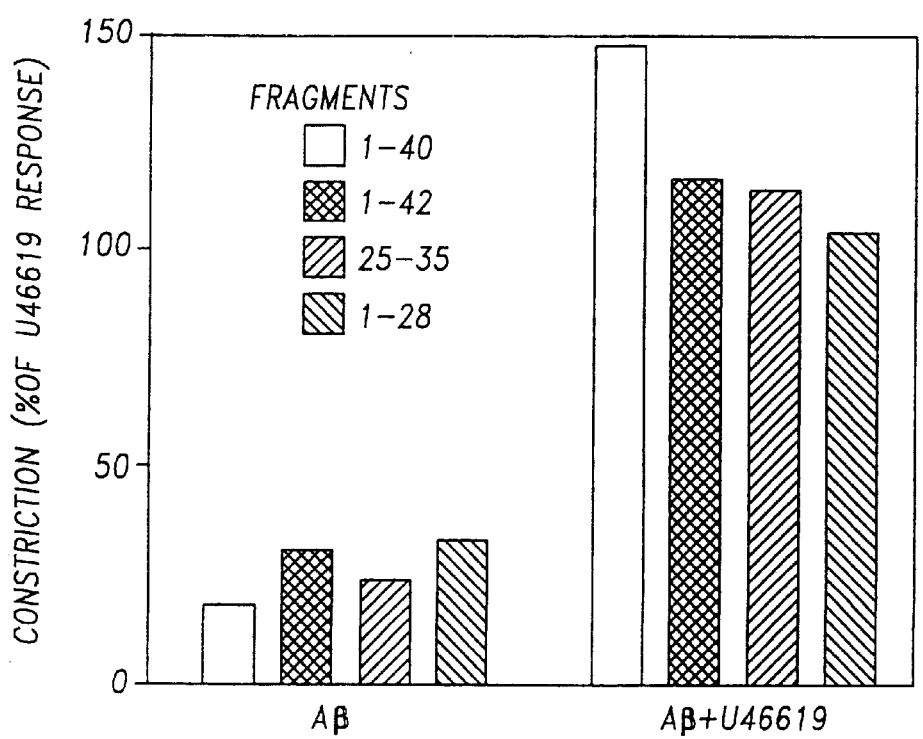
Figure 18:
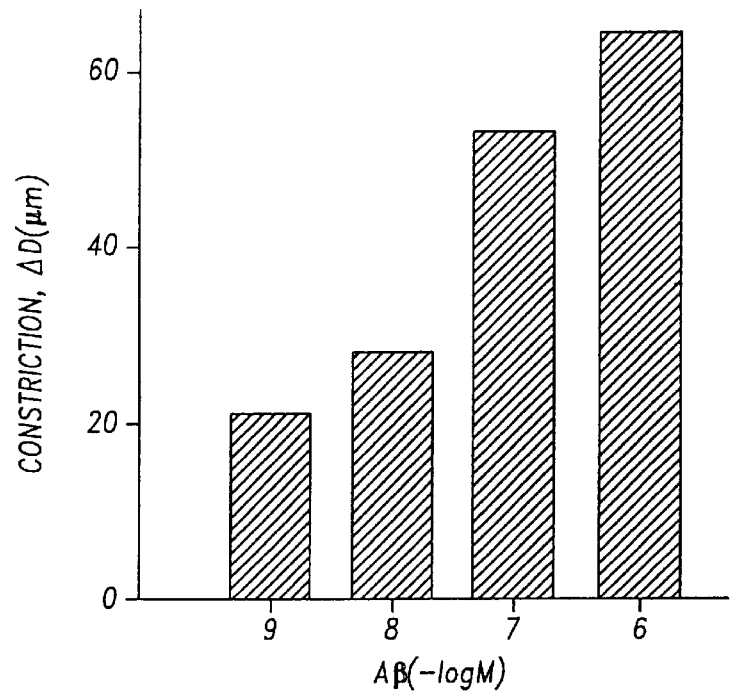
Figure 19:
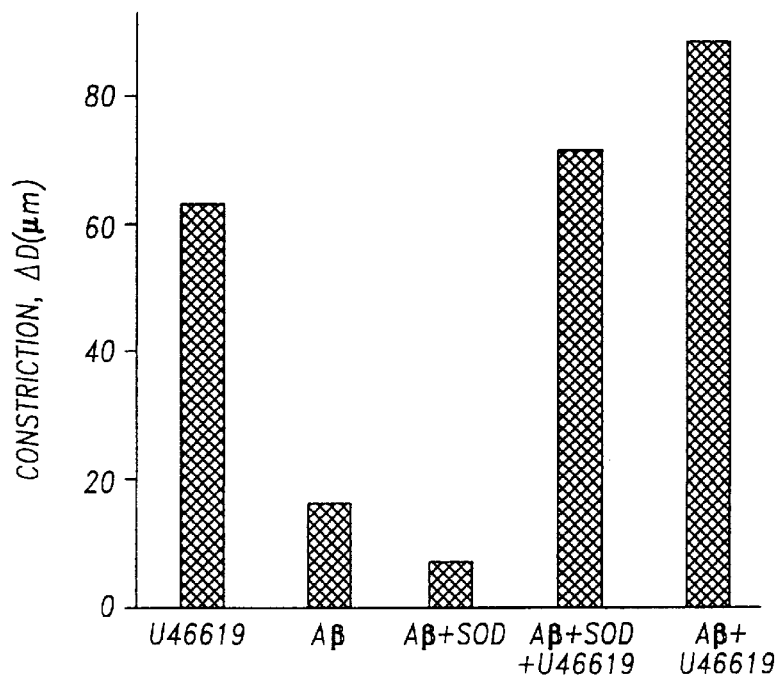
Figure 20:
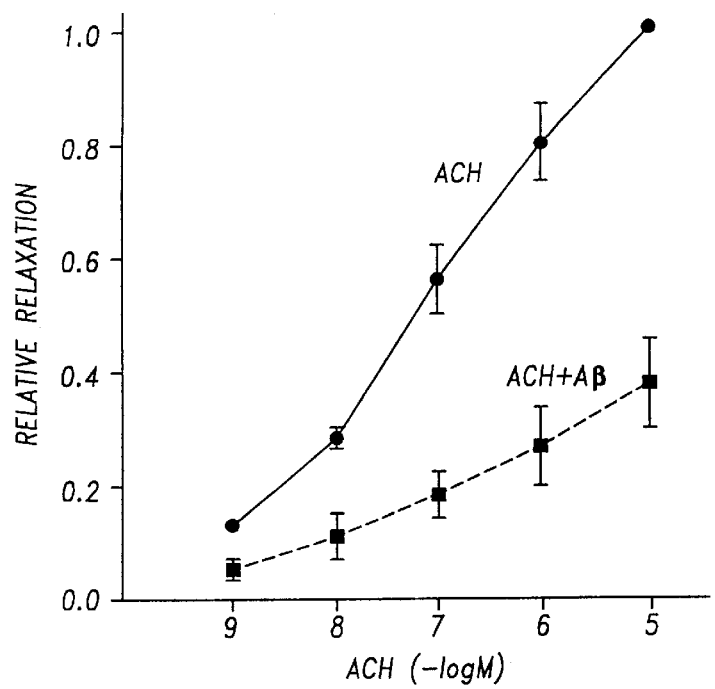
Figure 21A:
Figure 21B:
Figure 21C:

(B) Control aorta at a magnification of 9,500 showing an intact endothelial cell adhering to the internal elastic lamina, organelles clearly visible in the cytoplasm include the nucleus, mitochondria, and golgi apparatus, a tight junction can be seen between the endothelial cell and adjoining cell;

(C) Aortic ring treated with β-amyloid at a magnification of 4,000, visible features include derangement of the endothelial cell layer, a condensed nucleus to the left, separation from the internal elastic lamina and in areas denuded internal elastic lamina;

(D) Aortic ring treated with B-amyloid at a magnification of 7,000, at this magnification endothelial damage is clearly visible with cytoplasm and membrane destruction as well as swollen mitochondria and no other recognizable organelle;

(E) Aorta pretreated with SOD prior to the addition of β-amyloid (magnification 4,000), two intact endothelial cells closely adhering to the internal elastic lamina are observed;

(F) Aortic ring pretreated with SOD and then treated with β-amyloid (magnification 8,000), this higher magnification reveals an endothelial cell with normal features adhering to the internal elastic lamina close to a fenestration, intact organelles such as nucleus, mitochondria, and rough endoplasmic reticulum are observed, a tight junction can also be seen with the adjacent cell;

FIG. 15 is a histogram illustrating the effect of β-amyloid peptide ($A\beta_{40}$) and the vasoconstrictor thromboxane $A_2$ on the constriction of rat coronary arteries;

FIG. 16 illustrates real time recording of coronary artery vasoactivity induced by β-amyloid peptides wherein $A=A\beta_{1-40}$, $B=A\beta_{25-35}$, and $C=A\beta_{1-128}$;

FIG. 17 is a histogram illustrating the constriction of rat coronary arteries by various amyloid fragments;

FIG. 18 is a histogram illustrating the effect of increasing concentrations of amyloid peptide ($A\beta_{40}$) on coronary artery constriction induced by $10^7$M U46619;

FIG. 19 is a histogram illustrating the action of the oxygen radical scavenging enzyme superoxide dismutase (SOD) on $10^{-6}$M $A\beta_{40}$ induced constriction of coronary arteries;

FIG. 20 is a graph illustrating the effect of pretreatment of coronary arteries with a single dose ($10^{-6}$M) of $A\beta_{40}$ on acetylcholine induced relaxation;

FIGS. 21A–C are electron micrographs showing endothelial cell layers in rat coronary arteries, (A) Control coronary artery with normal endothelial cells closely adhering to the intimal elastic lamina lining of the lumen, (B) Coronary artery treated with β-amyloid for thirty minutes at 10-6M, and (C) Coronary artery pretreated with SOD (150 units/ml) thirty seconds prior to the addition of β-amyloid wherein intact endothelial cells with normal appearance and closely adhering to the internal elastic lamina are observed;

DETAILED DESCRIPTION OF THE INVENTION

Generally, the present invention provides a method for preventing diseases wherein at least one of the causes of the disease is β-amyloid peptide induced free radical production resulting in vascular endothelial dysfunction and/or destruction and vasoactivity by antagonizing vascular free radicals in excess of functional equilibrium.

It is well known that both β-amyloid peptide and free radicals are produced normally and exist in functional equilibrium and are part of the normal, homeostatic state of physiology in animals. The exact functional roles of β-amyloid peptide and free radicals in the normal physiological and biochemical activities of an animal are not completely known. However, as discussed in detail below, β-amyloid peptide has been found to cause or induce imbalances in the normal or homeostatic levels of free radicals present in an organism. That is, β-amyloid peptide has been shown to shift the normal equilibrium or induce imbalance in the equilibrium of free radicals present in cells (specifically vascular cells). This excess of free radicals is over and above the functional equilibrium present during normal homeostasis. Such levels could be measured by a number of means, but are directly observed in the experimental set-up described herein [Byung Paul Yu (1994); Prashar et al. (1993)].

In Alzheimer's disease an abnormal excess or accumulation of β-amyloid peptide is thought to be due to either overexpression or altered processing of amyloid precursor protein (APP). An excess of β-amyloid peptide as shown by applicants could rapidly lead to the conditions associated with an imbalance in free radical production leading to vasoconstriction and vascular endothelial destruction.

As a result of the increasing level of β-amyloid peptide induced free radicals, in excess of the functional equilibrium, endothelial dysfunction, which may include destruction, and vasoactivity, such as vasoconstriction results. The effects of β-amyloid peptide induced free radical production resulting in endothelial dysfunction and vasoactivity is an irreversible mechanism. That is, once vasoconstriction and endothelial destruction have occurred, the damage cannot be reversed or corrected either naturally or by way of medical or pharmaceutical intervention. As shown in the results below, in small relatively low concentrations, β-amyloid peptide can cause vascular endothelial dysfunction which may be reversible. The data below demonstrate that at low β-amyloid concentrations there is a shift in the relaxation response of vessels which is indicative of a reversible mechanism or response. Since reversibility based on vascular effects is already known, the initiation or progression of disease processes may be prevented or significantly ameliorated. Hence, a therapeutic regimen is developed but it must be a preventative of the endothelial destruction. It must act on the sequence of events preceding the vascular endothelial destruction, such as at β-amyloid production or binding, superoxide formation, etc., as discussed below.

By dysfunction it is meant that a normal function of the vascular endothelium is disrupted or ceases to function such as altered metabolism or cellular death.

The term vasoactivity includes vasoconstriction, vasodilation, and any other alterations in the vessel induced by β-amyloid peptide.

The diseases which may be prevented according to the method of the present invention include vascular diseases, physiological diseases related directly to blood flow, or neural diseases and are not limited to chronic diseases such as Alzheimer's Disease, Cerebral Amyloid Angiopathy, Vascular Dementias, Heart Diseases and vascular dementias (transient vascular incidents), and other more acute diseases to which vascular dysfunction is associated such as migraine headaches, arthritis, kidney disease, penile erection, tumor, localized pain, head injury induced conditions [Goldman reference], and other acute diseases or conditions known to those skilled in the art. For example, the vasoconstricting function of β-amyloid peptide can be used to locally constrict or reduce blood flow in order to retain and/or increase the localized concentration of analgesics in order to treat localized pain. Similarly for other conditions, β-amyloid peptides can be administered to alter or restrict localized blood flow to enhance the therapeutic effects of drugs given to treat a specific condition by acting as a barrier to blood flow. Alternatively intravenous β-amyloid administration, guided for instance by angiography, could prevent blood loss from a bleeding vessel.

β-amyloid has also been shown to sensitize blood vessels to vasoconstrictors both in vitro and in vivo. This phenomenon can be used to enhance the effects of vasoconstrictors administered to a subject.

The term antagonizing is used in its broadest sense. Antagonism can include any mechanism or treatment which results in inhibition, inactivation, blocking or reduction in the β-amyloid peptide induced mechanism of free radical production which results in the endothelial dysfunction and vasoactivity or in the actual level of free radicals. For example, the antagonizing step can include inactivating the free radical excess induced by β-amyloid peptide. For free radicals expressed in excess of the functional equilibrium, interventions can be established which inactivate the excess free radicals, such as exposure of the free radicals to antioxidants or free radical scavengers. Excess free radicals induced by β-amyloid peptide can be locally inactivated, quenched, and/or converted to less harmful compounds. The effect of excess oxygen free radicals produced within endothelial cells as a result of β-amyloid peptide exposure can be quenched, inactivated, and/or reduced using a free radical antagonist to reestablish the functional equilibrium.

Additionally, the functional equilibrium can be reestablished and/or maintained by inhibiting free radicals synthesis [Byung Paul Yu (1994); Janssen et al. (1993)].

Vascular free radical production induced by β-amyloid, which results in excess over functional equilibrium, can also be antagonized by inhibiting either or both β-amyloid synthesis and β-amyloid binding to the affected cells, such as endothelial cells. As described below, for therapeutic purposes where it is desired to either inhibit or prevent the effects of β-amyloid peptide, the endothelial cells (vessel) would be exposed to antagonists to either β-amyloid production or the effects of β-amyloids such as recognized β-amyloid antagonists, antioxidants, free radical scavengers, and nitric oxide compounds. Additionally, blocking of β-amyloid receptors on the target cells can be contemplated by the present invention.

Furthermore, the functional equilibrium may be reestablished and/or maintained by correcting the root causes of APP overexpression or altered processing.

Applicants acknowledge that other causes may exist for the diseases discussed above, however, the method of the present invention provides a therapeutic regimen which can be used to treat a central cause of many of these diseases [Olanow (1993); Offermann (1994)].

The general cascade or mechanism for β-amyloid induced free radical production resulting in irreversible endothelial cell death include the general steps of binding of β-amyloid to the surface of an endothelial cell causing vessel constriction. The result of the β-amyloid induced vessel constriction is a lack of oxygen and nutrients to the tissue supplied by the vessel (endothelial cell). The binding or interaction of β-amyloid with the endothelial cell induces the production of excess free radicals over and above the functional equilibrium which causes the irreversible endothelial cell damage and finally death. Therapeutic intervention to prevent diseases which are caused, in part, by β-amyloid can be undertaken at any step of the cascade as described above.

It should be emphasized that since the effects of β-amyloid induced endothelial dysfunction and/or and vasoactivity are irreversible, that, in order to prevent diseases wherein at least one of the causes of the disease is β-amyloid induced free radical production, intervention must be undertaken as early as possible to prevent further endothelial damage or to prophylactically prevent the onset of endothelial damage. Clinical manifestations of diseases caused by β-amyloid induced free radical excess appear to take on the order of years to decades to surface.

Therefore, early detection of those individuals who are genetically susceptible or whose free radical equilibrium is imbalanced due to excess free radical production by other means will be critical to initiating early and effective prophylactic treatment in order to prevent the irreversible endothelial damage which may occur years or decades later.

Since many of these diseases have a genetic component, persons at risk and in need of prophylactic treatment can be identified by genetic screening as is known in the art for genetic aberrations such as mutations in β-amyloid genes (Chromosome 1, 14, 19, and 21) and other aberrations such as translocations of genes or chromosomes. One such marker is the ε4 allele of Apolipoprotein. This marker has been implicated as a determinant of individuals who may be predisposed to Alzheimer's Disease. Because of the link between Alzheimer's Disease and β-amyloid, those individuals who test positive for the ε4 allele and/or the other genetic aberrations listed above or known to those skilled in the art would be candidates for prophylactic treatment as discussed above.

Additionally, the present invention provides a method of producing a vasoactive effect by exposing a vessel having an intact endothelium to a β-amyloid peptide. The present invention utilizes for the first time a direct vasoactive effect of β-amyloid peptides on blood vessels.

By vasoactive effect, it is meant that exposure of a vessel having intact endothelium will contract when exposed to β-amyloid peptide (or agonists). Unless there is pretreatment of the vessel, this effect has been found to be irreversible as discussed in detail below. This effect can be modified or inhibited by pre-exposure of the vessel to an antagonist of the cascade steps which comprise the mechanism of action of β-amyloid peptide on the vessel or by pre-treatment with a vasoconstrictor.

The term exposing is used in its broadest sense. Exposure can take place in a tissue bath for a diagnostic purpose, in vivo for therapeutic purpose, or ex vivo for various other treatment purposes. Therefore, exposing denotes the addition of β-amyloid peptide (or agonist) to a bath containing the blood vessel, or administration in an appropriate carrier, such as orally, parenterally and by other means well known in the art.

For therapeutic purposes wherein it would be desirable to either inhibit or prevent the effects of β-amyloid peptide, as detailed below, the vessel is exposed to antagonists to the effects of β-amyloids, such as recognized β-amyloid antagonists, anti-oxidants, free radicals scavengers, and nitric oxides compounds, well known in the art. A partial list of these compounds include antioxidants (ascorbic acid, α-tocopherol, carotenoids, methylprednisolone, 21-aminosteroids); free radical scavengers (superoxide dismutase (SOD), SOD-mimicking compounds, monoamine oxidase inhibitors), nitric oxide producing compounds (nitroglycerin, sodium nitroprusside, glycerol trinitrate, glutamate) and other stimulants of NO synthesis.

For example, a peptide antagonist of β-amyloid peptide (in a suitable vehicle) such as NADPH-dependent oxidoreductase is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art including, but not limited to, increased survival and improved survival rate or length and other indicators as are selected as appropriate measures by those skilled in the art.

In the method of the present invention, the peptide antagonist of β-amyloid peptide can be administered in various ways. It should be noted that the peptide antagonist or β-amyloid peptide can be administered as the compound or as pharmaceutically acceptable salt and can be administered alone or in combination with pharmaceutically acceptable carriers. The compounds can be administered orally, subcutaneously or parenterally including intravenous, intraarterial, intramuscular, intraperitoneally, skin patches and intranasal administration. Implants of the compounds are also useful. The patient being treated is a warm-blooded animal and, in particular, mammals including man.

When administering the peptide antagonist of β-amyloid peptide parenterally, the peptide antagonist of β-amyloid peptide will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the peptide antagonist of β-amyloid peptide can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

A pharmacological formulation of the peptide antagonist of the β-amyloid peptide utilized in the present invention can be administered orally to the patient. Conventional methods such as administering the compounds in tablets, suspensions, solutions, emulsions, capsules, powders, syrups and the like are usable. Known techniques which deliver the peptide antagonist orally or intravenously and retain the biological activity are preferred.

For delivery within the CNS, pharmacological formulations that cross the blood-brain barrier can be administered. [Betz et al., 1994; Brem et al., 1993] Such formulations can take advantage of methods now available to produce chimeric peptides in which the present invention is coupled to a brain transport vector allowing transportation across the barrier. [Pardridge, et al., 1992; Pardridge, 1992; Pardridge, et al., 1993]

In one embodiment, the peptide antagonist of β-amyloid peptide can be administered initially by intravenous injection to bring blood levels to a suitable level. The patient's blood levels are then maintained by an oral dosage form, although other forms of administration, dependent upon the patient's condition and as indicated above, can be used. The quantity of peptide antagonist to be administered will vary for the patient being treated and will vary from about 100 ng/kg of body weight to 100 mg/kg of body weight per day and preferably will be from 10 μg/kg to 10 mg/kg per day.

As demonstrated by the experiments below, β-amyloid, which has already been implicated as a key factor in the pathophysiology of Alzheimer's disease, has a direct vasoactive effect on blood vessels. This effect is produced in nanomolar concentrations, much lower in concentrations used in previous studies showing effects such as calcium homeostasis [Mattson et al., 1993], but similar to those showing toxicity [Yankner et al., 1990] or induction of potassium channels. Accordingly, in concentrations lower than between 10 μM and 80 μM, vasoconstriction is shown as a direct result of β-amyloid exposure, these levels being similar to those which produce toxic effects. Hence, there is no issue that the vasoconstrictive effects are shown at the same levels which also show cellular toxicity.

As shown in the experimental data below, the vasoactive effect is demonstrated in less than five minutes. In contrast, in reports of neurotrophic and toxic effects [Yankner et al., 1990] of β-amyloid, incubation periods of two to four days were required to demonstrate an effect. Finally, the effects of β-amyloid are shown herein on intact tissue with intact permeability barriers and cell to cell interaction. Hence, there is no issue as to whether or not the present invention can be applied at a tissue level.

In vivo models of diseases caused at least in part by β-amyloid induced free radical production in excess of functional equilibrium and neurodegenerative disease in animals predisposed to neurodegeneration can be produced according to the present invention as in transgenic animals or cell lines with mutations in genes for dealing with free radicals, such as superoxide dismutase mutations, mutations in β-amyloid genes, or other mutations such as Apo E mutations, and SOD mutations. Animal models can be produced by intravascular administration of β-amyloid, as described herein, or by production of transgenic animals, such as mice, by methods known in the art. Cell models can be produced by transfection or by other methods known in the art. These models can be used for drug screening purposes in the search and development of treatments for the diseases or conditions caused by these mutations.

The present invention provides for transgenic gene and polymorphic gene animal and cellular (cell lines) models as well as for knockout models. These models are constructed using standard methods known in the art and as set forth in U.S. Pat. Nos. 5,387,742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information.

The data generated and set forth below demonstrates that the action of β-amyloid is mediated through the dysfunction and/or destruction of the vascular endothelium of the vessels. Pharmacologically, β-amyloid is shown to be an effective antagonist of acetylcholine induced relaxation of blood vessels. Washing the blood vessels did not remove the effect of β-amyloid indicating that constituents of the endothelium were permanently altered by the β-amyloid.

The following experiments demonstrate the mechanism of action of β-amyloid on vasoactivity as well as provide a basis for the utility of the present invention. The data shows 1) The causal link between β-amyloid, vasoconstriction, superoxide products, and endothelial cell damage, as well as; 2) the causal link between β-amyloid and the resultant vascular disease caused thereby; 3) the causal link between β-amyloid and further neurological disorders; and 4) therapeutic means of breaking or antagonizing the aforementioned causal links providing a basis for prophylactic treatment.

METHODS

Preparation of blood vessels:

Freshly excised rat and porcine blood vessels were placed in Kreb's bicarbonate buffer equilibrated with 5% $CO_2$ in $O_2$. The buffer composition consisted of 118.2 mM NaCl, 4.7 mM KCl, 1.2 mM $MgSO_4$, 2.5 mM $CaCl_2$, 1.2 mM $NaH_2PO_4$, 23 mM $NaHCO_3$ and 11.2 mM glucose. After cleaning the vessels free of fat and other adhering tissues, the vessels were cut into ring segments of approximately 3mm in length. Care was taken not to damage the intimal surface.

The endothelium was removed from some preparations by rubbing the inside of the lumen with a metal spatula for six to ten seconds and subsequent rinsing with buffer. The removal of endothelium was confirmed by testing for relaxation to acetylcholine [Furchgott and Zawadzki, 1980].

Measurement of vascular response:

The blood vessel preparations were mounted on stainless steel hooks attached to a force-displacement transducer and equilibrated under the optimum tension of 1.3 g for a period of sixty minutes in a tissue bath (10 ml) containing oxygenated (5% $CO_2$ in $O_2$) Kreb's buffer at 37° C. The buffer was changed every fifteen minutes. After equilibration for sixty minutes the viability of the blood vessel with intact endothelium was established by constricting the blood vessel using phenylephrine (1 mM). This dose of phenylephrine elicited 80% of the maximum response. Subsequent addition of acetylcholine demonstrated the characteristic relaxation of blood vessel. The vessel preparations were washed for fifteen minutes before various manipulations as described below.

RESULTS

Figure 1A:
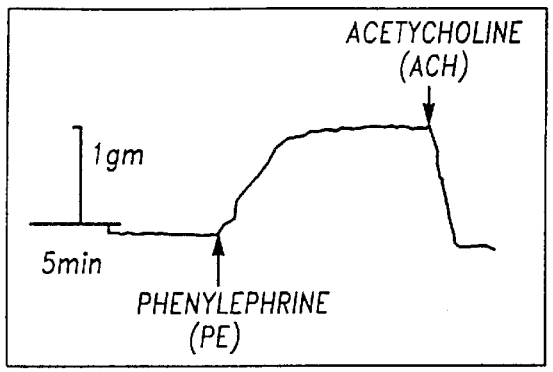
FIG. 1a is a graph of response, over time, of blood vessels with intact endothelium wherein phenylephrine induces constriction and acetylcholine produces relaxation.
Figure 1B:
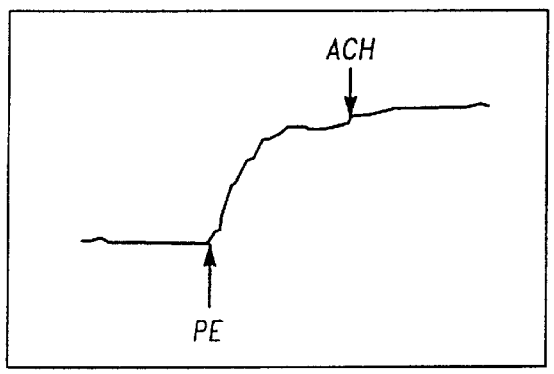
FIG. 1b is a similar graph showing the response of a blood vessel without endothelium, acetylcholine failing to produce relaxation of a pre-constricted blood vessel.
Figure 2A:
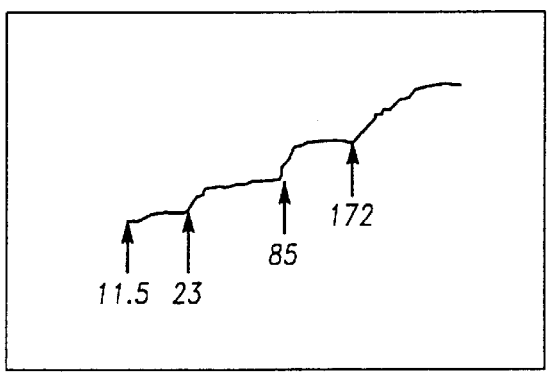
FIG. 2a is a graph showing the effect of β-amyloid on basal tension by increasing the concentration of β-amyloid to a muscle preparation, β-amyloid inducing constriction of the blood vessel.
Figure 2B:
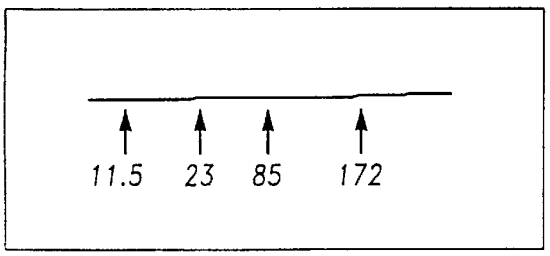
FIG. 2b shows the effect of β-amyloid on a blood vessel without endothelium.
Figure 10:
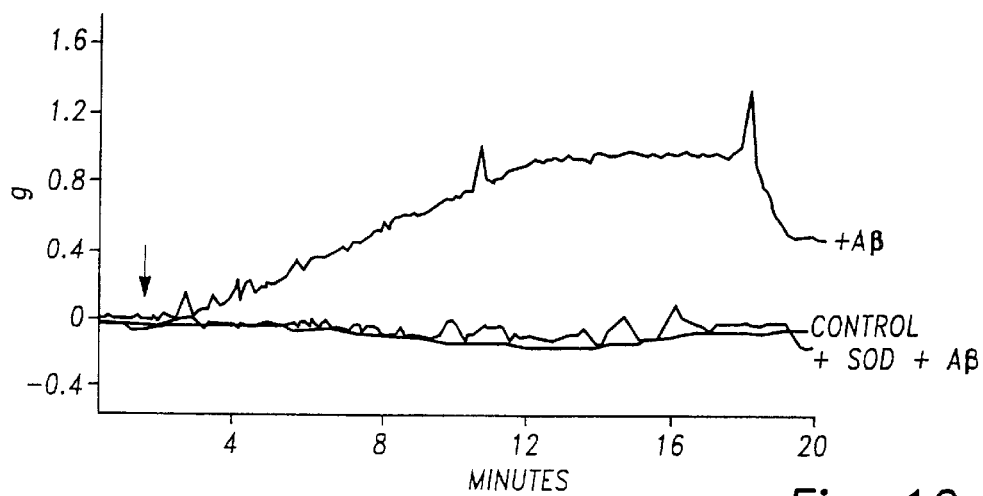
FIG. 10 is a graph showing β-amyloid induced contraction of blood vessels with intact endothelium.

The blood vessel constricted in response to phenylephrine with or without endothelium, as shown in FIGS. 1 and 10. Acetylcholine released nitric oxide and relaxed preconstricted vessels only when endothelium was present.

β-amyloid constricted the blood vessel in a concentration-dependent manner. The constricting effects of β-amyloid only occurred in the presence of endothelium as shown in FIG. 2. This indicates that the action of β-amyloid is mediated via the endothelium.

Figure 3:
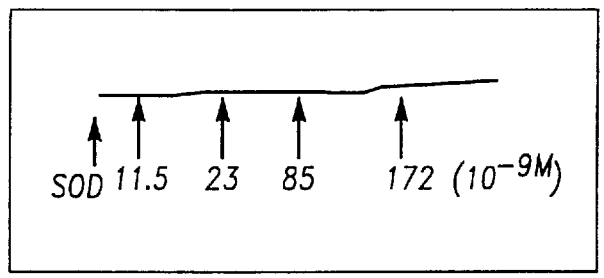
FIG. 3 is a graph showing the effect of the addition of 180 units of superoxide dismutase (SOD), the SOD blocking the vasoconstriction induced by β-amyloid.

To investigate the possible role of superoxide anion in mediating the vasoconstriction elicited by β-amyloid, superoxide dismutase enzyme (SOD) was added (180 units) to the bioassay bath thirty seconds before the addition of β-amyloid. Pretreatment with SOD eliminated the vasoconstriction produced by β-amyloid as shown in FIG. 3. This indicated that the vasoconstriction elicited by β-amyloid may be due to its effect on superoxide formation.

Figure 4:
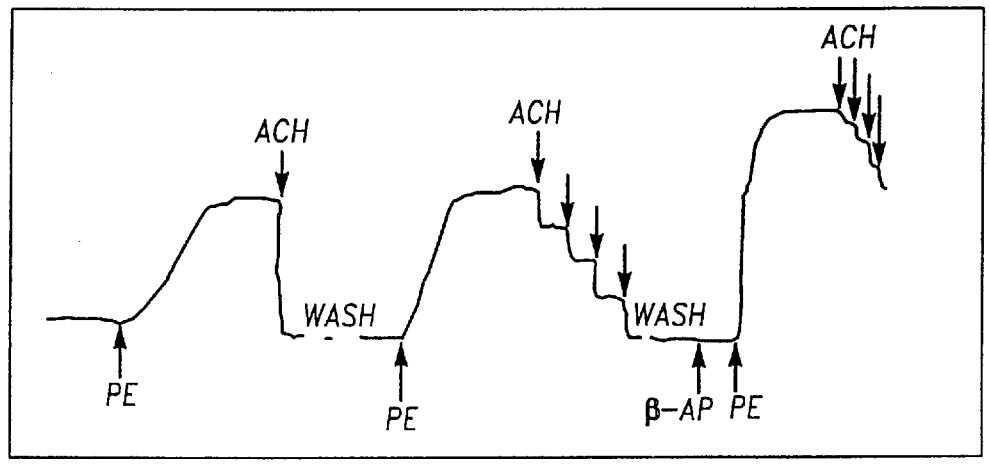
FIG. 4 is a graph wherein the blood vessel was first tested with large doses ($1 \times 10^{-4}$M) of acetylcholine for endothelia presence, the preparation was then tested with small doses of acetylcholine cumulatively, the muscle was pre-treated with β-amyloid shows enhanced constriction and significantly reduced relaxation induced by same doses of acetylcholine, washing the preparation did not restore the relaxation to the preparation.

FIG. 4 shows a blood vessel preparation with intact endothelium. The vessel was constricted by phenylephrine and relaxed by acetylcholine. The washed tissue was then tested with smaller doses of acetylcholine cumulatively. Pretreatment with β-amyloid enhanced constriction and significantly reduced relaxation induced by the same doses of acetylcholine. Washing the above preparation following exposure to β-amyloid did not restore the acetylcholine induced relaxation indicating the system was irreversibly affected by β-amyloid treatment.

Figure 5:
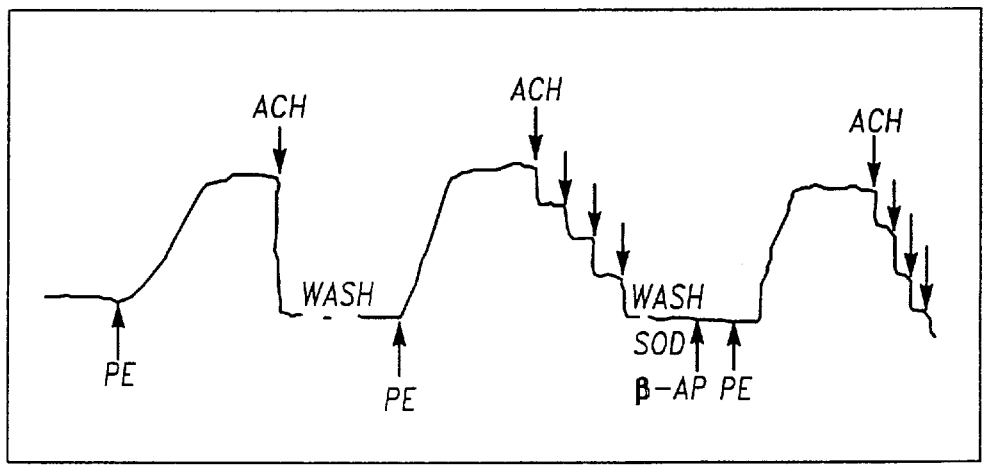
FIG. 5 is a graph showing the results of an experiment conducted as described in FIG. 4, therebeing treatment with the enzyme SOD which totally eliminated the effect of β-amyloid.

Pretreatment with the enzyme SOD almost totally removed the inhibitor effect of β-amyloid as shown in FIG. 5.

Figure 6:
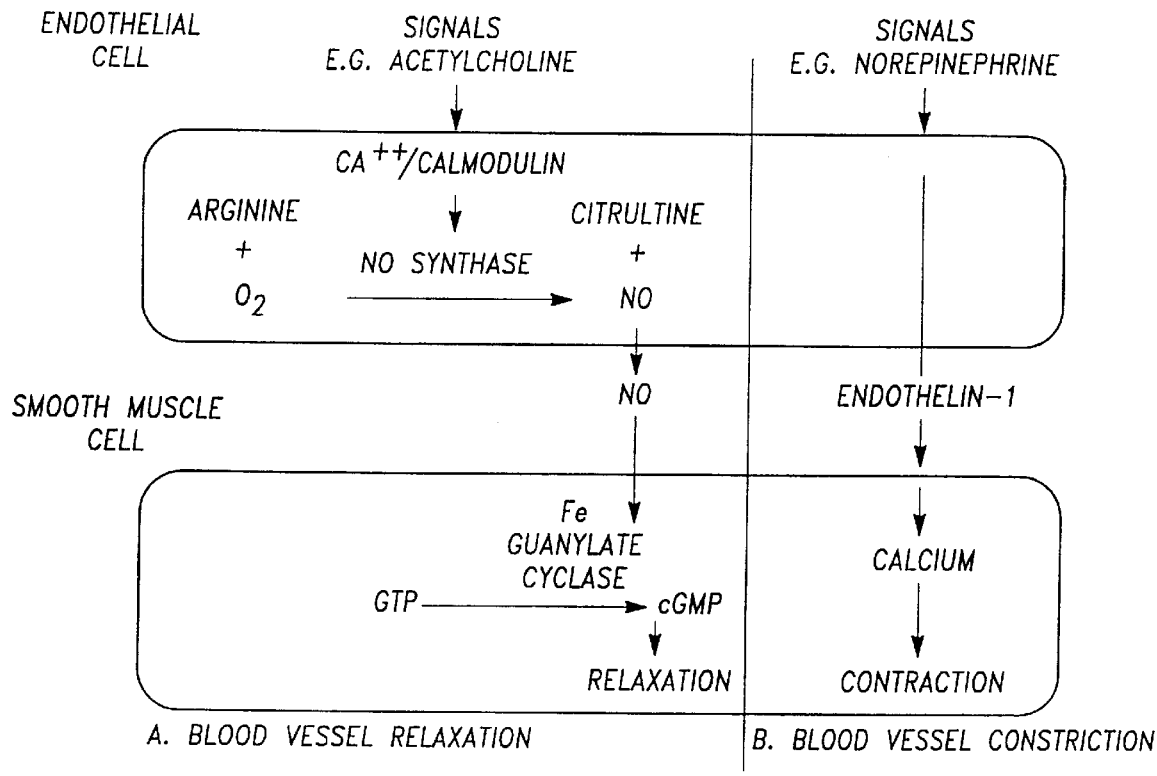
FIG. 6 is a flow chart showing the sequence of reactions leading to relaxation and contraction of blood vessels wherein A shows the endothelia derived relaxing factor, nitric oxide (NO) diffuses to the muscle cells, stimulating the production of cyclic GMP and further induces relaxation of the smooth muscle, B shows contraction of smooth muscle mediated by calcium and being stimulated by endothelium derived contracting agents such as endothelin-1.
Figure 7:
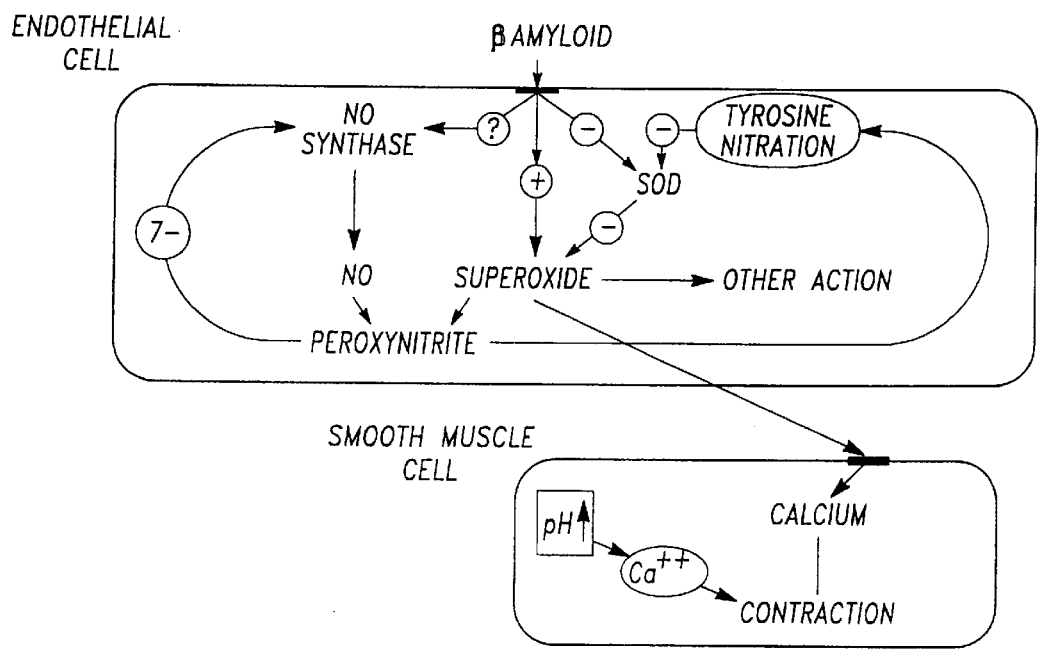
FIG. 7 is a flow chart showing the action of β-amyloid on endothelial cells, β-amyloid caused muscle contraction and prevented relaxation possibly via (1) effects on endothelial nitric oxide synthase or
(2) inhibition of superoxide dismutase (SOD) or
(3) producing a relative excess of superoxide radicals which cause
   (a) destruction of nitric oxide,
   (b) activation of calcium entry into muscle cell, and
   (c) elevation of muscle pH and release of calcium form intracellular stores.
Figure 8:
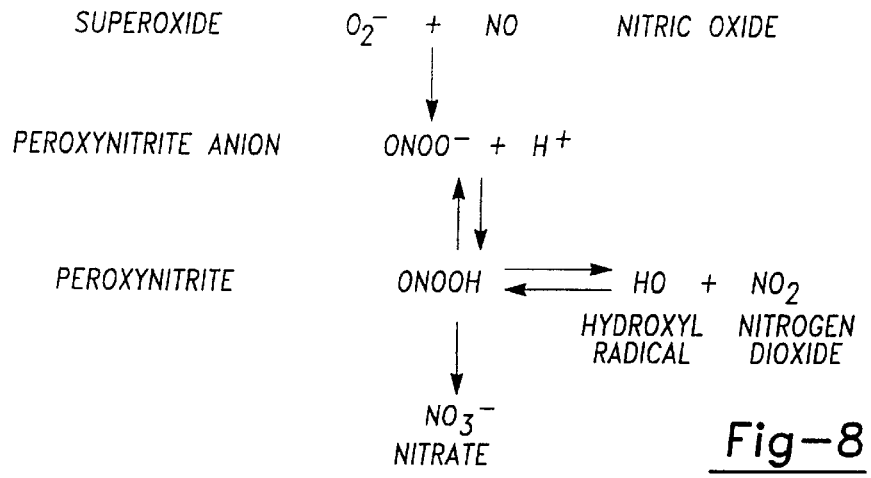
FIG. 8 is a flow chart showing the production of destructive radicals by the reaction between superoxide and nitric oxide, peroxynitrite is broken down to produce the highly reactive hydroxyl radical, nitrogen dioxide and nitronium ion, all of which can be neurotoxic.

The results show that the vasoconstriction elicited by β-amyloid is mediated by superoxide anion, which is known to inactivate endothelium derived relaxing factor, nitric oxide as shown in FIG. 6. However, it is not clear whether there is increased superoxide production or decreased superoxide destruction. The fact that the effect is maintained after β-amyloid washout also suggests that the relative increase is due to altered enzymatic activity. One possibility is illustrated in FIG. 7 showing that β-amyloid inhibits the endothelial nitric oxide synthase (eNOS) thereby reducing the level of nitric oxide available to interact with superoxide. Alternatively β-amyloid may increase superoxide production from eNOS or alter the balance in rate of production of superoxide and nitric oxide or the redox state of the latter. Nitritic oxide produced in a reduced form (NO) has a high affinity for superoxide and rapidly forms peroxynitrite, a powerful neurotoxic oxidant: $NO+O_2^--ONO_2^{31}$ as shown in FIG. 8. As a consequence of loss of NO, smooth muscle vasodilatation is lost. Thus, this response is abolished by SOD and competes with ACH mediated vasodilatation which is mediated via NO production.

Alternatively, β-amyloid may inhibit SOD directly or indirectly. One mechanism by which SOD is known to be permanently inactivated is via the peroxynitrite ion. This is known to react with transition metals to produce a nitronium-like intermediate which can nitrate tyrosine residues. The copper containing SOD catalyses nitronium ion production and undergoes tyrosine nitration and consequent inactivation [Beckman et al., 1993]. Other enzymes, including NOS, might be similarly nitrated by peroxynitrite. Nitrosylation of the NMDA redox modulatory site prevents calcium mediated neurotoxicity and may be one of the mechanisms by which β-amyloid confers neuroprotectivity [Lipton et al., 1993].

Alternatively, it is possible that β-amyloid rapidly stimulates the increased formation of the superoxide radical via enzymes other than eNOS in vascular endothelium. A number of enzymes (some of them specific to endothelium) are known to produce superoxide as a normal product i.e., eycloxygenase, lipoxygenase, prostaglandin hydroperoxidase and others [Betz, 1993] including nitric oxide synthase itself [Pou et al., 1992].

The superoxide radical will have several effects resulting in the observed vasoconstriction. Interactions occur with endothelial derived relaxing factor-nitric oxide. Superoxide will not readily diffuse through cell membranes although some cell types allow its passage via anion channels. If it reaches the smooth muscle cells it will cause stimulation of direct entry of calcium into smooth muscle cells. Several investigators have examined the effect of superoxide radical on intracellular calcium levels. In myometrial cells, calcium entry is directly facilitated by superoxide which opens calcium channels [Hirosumi, 1988]. Indirect release of calcium from intracellular stores occur. The entry of superoxide into muscle cells results in the loss of intracellular protons. A rise in intracellular pH results in the release of intracellular calcium stores.

In addition to the loss of NO postulated by increasing levels of superoxide, the rise in intracellular calcium due to the above observed actions results in muscular contraction. Thus, the effect of superoxide production is predicted to cause the vasoconstriction observed.

The possibility that superoxide or other oxygen radicals serve physiological functions has been suggested by Rosenblum [1983], who noted reversible dilation of cerebral microvessels in response to oxygen free radicals. Kontos et al. [1984] observed that oxygen radicals mediated the cerebral arteriolar vasodilatation that occurs in response to arachidonic acid and bradykinin. This effect was not mediated by endothelium derived relaxing factor produced in response to bradykinin [Rosenblum, 1987]. More recently, it was proposed that superoxide is a contracting factor that may have direct effects on vascular smooth muscle [Katusic and Vanhoutte, 1989]. Both the vasodilator response observed by Kontos et al. [1984] and its effect observed by Katusis and Vanhoutee [1989], involved arachidonic acid metabolism and led these investigators to suppose that some of the vasoactive properties previously attributed to prostaglandins might be direct effects of superoxide.

It has also been previously suggested that superoxide may also modulate micro-vascular tone by controlling the level of nitric oxide. This is supported by the observed inactivation of nitric oxide by superoxide [Moncada et al., 1988; Sneddon and Vane, 1988], and the prolongation of the effect of nitric oxide by SOD in vivo.

It has also been previously suggested that superoxide is produced by the endothelium to serve as a physiological modulator of nitric oxide activity [Halliwell, 1989]. Oxygen free radical-mediated reversal of acetylcholine-induced vasodilatation in brain is believed to occur through this mechanism [Wei et al., 1985;Marshall et al., 1988]. Thus, the observations made herein are consistent with the current data on the vasoactive properties of superoxide. However, the finding that superoxide is quickly generated by endothelium in response to β-amyloid is novel. The generation or decreased destruction of superoxide caused by β-amyloid may have significance in number of disorders and diseases, particularly those associated with peripheral and central blood vessel disease and neurodegeneration as is discussed below.

The relationship between β-amyloid ($A\beta_{1-39-42}$) and oxygen radical formation was examined in a system known to respond physiologically to free radical endothelium mediated vasoactivity [Furchgott & Zawadski, 1980]. β-amyloid constricted the blood vessel and the vessel was sensitive to β-amyloid in the concentration range of $0.25-2.0 \times 10^{-6}$M (see FIG. 10).

Referring to FIG. 10, the arrow indicates the addition of $10^{-6}$M β-amyloid. The control tissue received no β-amyloid. SOD (150 units/ml) was added thirty seconds prior to the addition of β-amyloid. The maximum contraction induced by β-amyloid was 1.14±0.13 (g) and in presence of SOD the contraction was reduced to 0.04±0.02 (g). Values represent the mean ±SEM of five separate experiments.

The vasoactive property of β-amyloid occurred only in the presence of endothelium suggesting that this action is mediated via the endothelium. The β-amyloid induced vasoactivity had the following characteristics. The blood vessel showed an immediate response and vasoactivity was evident within thirty seconds. The initial detectable change was a minor relaxation of <0.1 g. This was followed by a series of contractions and relaxations. There were periodic bursts of contractions followed by immediate relaxations. This activity persisted for a period of fifteen to twenty minutes.

To investigate the role of oxygen radicals in mediating the vasoactivity elicited by β-amyloid, the superoxide scavenging enzyme superoxide dismutase (SOD) was added thirty seconds prior to the addition of β-amyloid. Pretreatment with SOD eliminated the vasoactivity induced by β-amyloid, suggesting that the vasoactive action of β-amyloid involves the formation of superoxide radicals. When SOD was added after incubation with β-amyloid, the vasoactivity was not abolished. Washing the tissue and removing the SOD without further addition of β-amyloid produced changes characteristic of endothelial dysfunction enhanced vasoconstriction and diminished vasodilation. Thus there was a continuous requirement for SOD to prevent the effects of β-amyloid. To ensure continued availability of SOD it was necessary to include SOD in the buffer used to rinse the tissue in the SOD treated preparation.

Figure 11A:
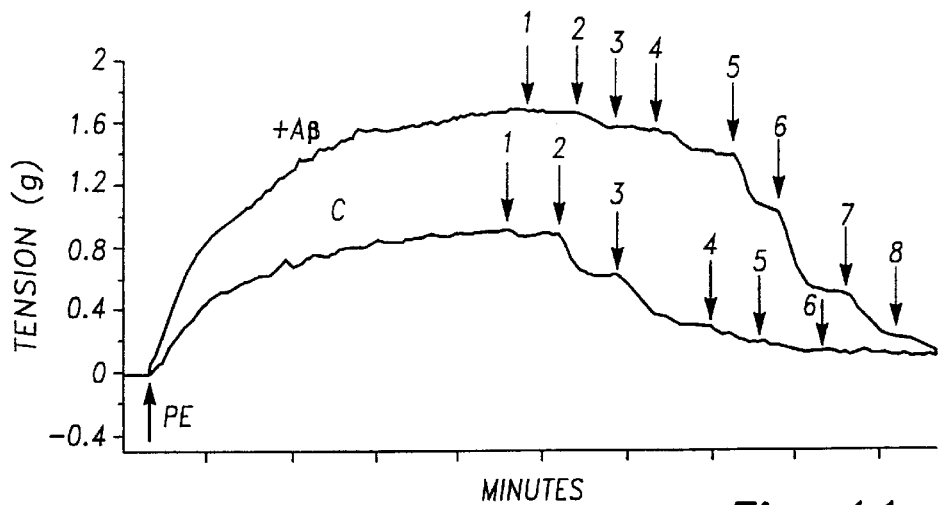
FIG. 11a is a graph showing the effect of pre-treatment of a blood vessel (rat aorta) with a single dose ($10^{-6}$M) of β-amyloid on relaxation induced by acetylcholine, as shown by the arrows, $1=10^{-9}$M, $2=10^{-8}$M, $3=5 \times 10^{-8}$M, $4=10^{-7}$M, $5=5 \times 10^{-7}$M, $6=10^{-6}$M, $7=10^{-5}$M, $8=5 \times 10^{-5}$M, the curve denoted by C is the control curve and +Aβ indicates the curve for β-amyloid treated aorta.
Figure 11B:
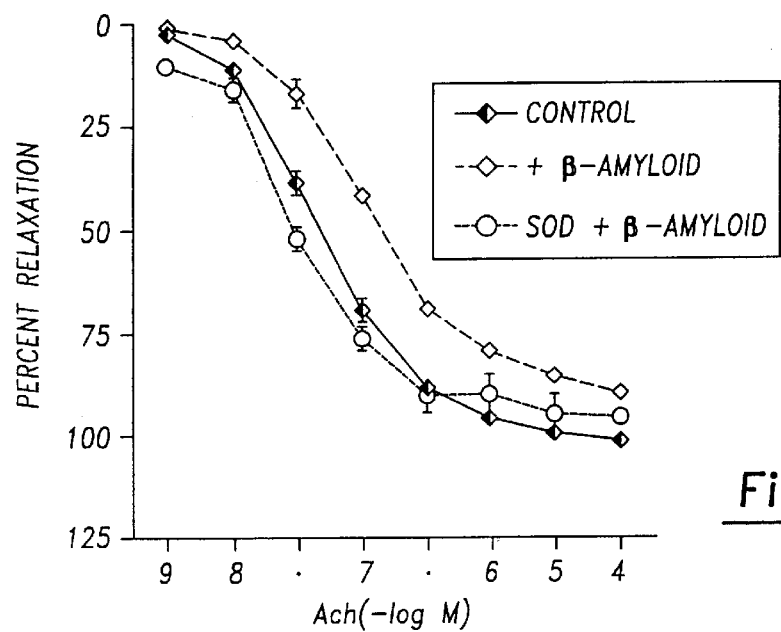
FIG. 11b is a graph showing percent relaxation of a blood vessel versus treatment of the blood vessel with acetylcholine.

Pretreatment with β-amyloid significantly reduced relaxation induced by the vasodilator acetylcholine as shown in FIGS. 11a and 11b.

As shown in FIG. 11a the aorta was preconstricted with $10^{-7}$M PE and relaxed with increasing doses of acetylcholine as shown by the arrows. ($1=10^{-9}$M, $2=10^{-8}$M, $3=5 \times 10^{-8}$M, $4=10^{-7}$M, $5=5 \times 10^{-7}$M, $6=10^{-6}$M, $7=10^{-5}$M, $8=5 \times 10^{-5}$M, the curve denoted by (C) is the control curve and +Aβ indicates the curve for β-amyloid treated aorta.)

FIG. 11b is a graph showing percent relaxation of a blood vessel versus treatment of the blood vessel with is acetylcholine; As shown in FIG. 11b, the aorta was preconstricted submaximally with $10^{-7}$M phenylephrine. FIG. 11b illustrates the relaxation by acetylcholine under control conditions and following fifteen minute incubation with $10^{-6}$M β-amyloid protein. The acetylcholine relaxation curve is shifted to the right but maintains its sigmoidal form indicating attenuation of acetylcholine induced relaxation. Values represent the mean ±SEM of 5 or more experiments. The cumulative percentage relaxation is significantly lowered by β-amyloid protein at all points past $10^{-8}$M acetylcholine. At higher doses of acetylcholine greater percentage changes in relaxation occur preserving the sigmoidal response. Pretreatment with SOD (150 units/ml) antagonized the effect of β-amyloid on acetylcholine induced relaxation.

Washing the tissue following β-amyloid treatment did not restore the acetylcholine-induced relaxation to control levels indicating that β-amyloid had altered endothelial function. The acetylcholine resistant S relaxation was overcome by the nitric oxide (NO) donor sodium nitroprusside (data not shown). Addition of SOD slightly potentiated the relaxation response to acetylcholine and at the same time antagonized the effect of β-amyloid.

Figure 12A:
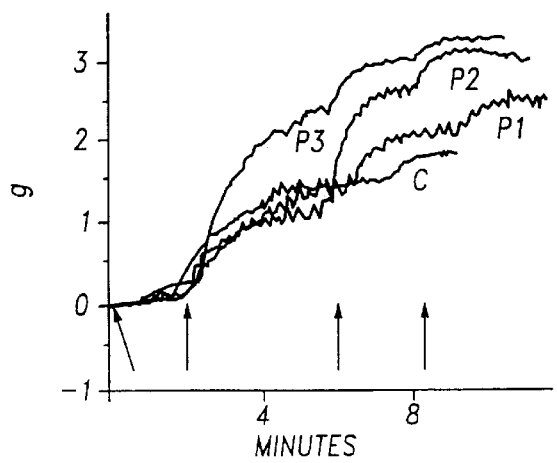
FIG. 12a is a graph showing the effect of β-amyloid on contraction and relaxation of blood vessel with intact endothelium.
Figure 12B:
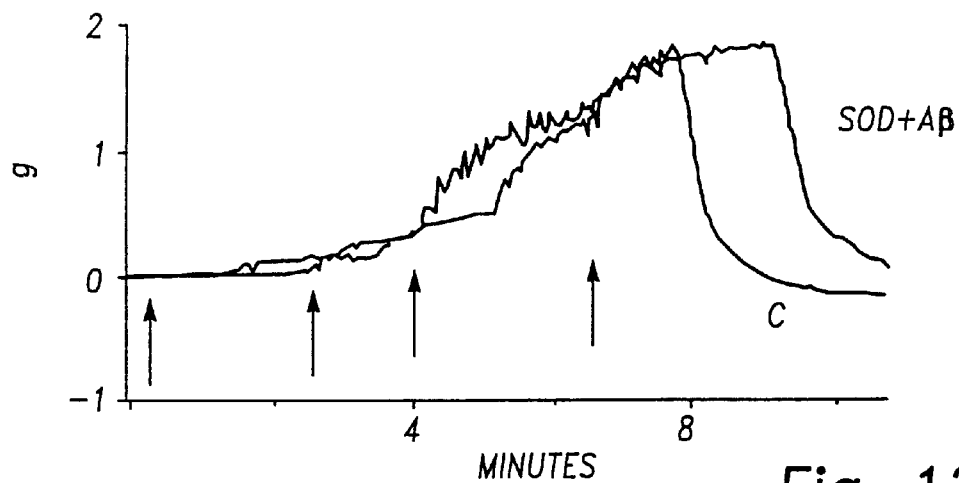
FIG. 12b is a graph showing the effect of SOD on β-amyloid ($10^{-6}$M) augmentation of PE induced contraction, (C) is the control curve without β-amyloid, SOD was added thirty seconds prior to the addition of $10^{-6}$M β-amyloid, and the arrows represent the points of addition of PE for the control.
Figure 12C:
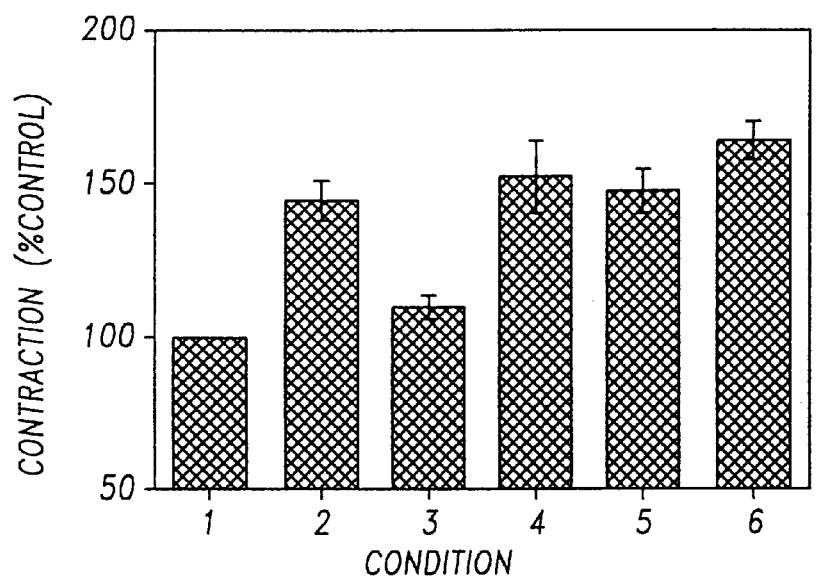
FIG. 12c is a histogram illustrating the specificity of SOD action by the use of active and inactive preparations of SOD.

FIGS. 12a–c show the enhancement of contraction induced by the vasoconstrictor phenylephrine (PE) following β-amyloid treatment.

As shown in FIG. 12a, control contraction with increasing concentrations of phenylephrine (2,4,8, and $16 \times 10^{-8}$M) is shown by trace C. The procedure was then repeated following incubation of the tissue with $10^{-6}$M β-amyloid for fifteen minutes (P1). The tissue was then rinsed and contractions repeated twice following fifteen minute incubation (P2 & P3) without further addition of β-amyloid. Statistical analysis of this data is shown in Table 1. Arrows are shown for points of addition for P3. Control incubations with buffer alone showed no increase with repeated contractions.

As shown in FIG. 12c, the aortic rings were preincubated with the appropriate test compounds before the addition of $10^{-6}$M -amyloid. Following a fifteen minute incubation, the preparations were contracted with $10^{-7}$M phenylephrine (PE) as described earlier. Control contractions with PE alone were carried out in presence of the various test compounds. Values represent the mean ±SEM of four or more experiments. The heat-inactivated SOD was prepared by placing it in boiling water for thirty minutes followed by cooling prior to use. The hydrogen peroxide-inactivated SOD was prepared by exposing SOD to 10 mM $H_2O_2$ for thirty minutes at pH 8.5 and subsequent separation using Microcon filtration system. The amyloid induced PE contraction was blocked by active SOD. Neither albumin or inactivated SOD had any effect on the amyloid activity.

Pretreatment with the enzyme SOD almost totally removed the enhancement of contraction by β-amyloid. Washing the tissue following treatment with β-amyloid and subsequent contraction with PE showed further increase indicating enhanced damage to the endothelium (see Table 1).

The effect of preincubation of blood vessel with $10^{-6}$M β-amyloid on contraction induced by phenylephrine (2,4,8, & $16\times10^{-8}$M is shown in Table 1). The maximum contraction in the absence of β-amyloid is taken as 100% and the values obtained following exposure to β-amyloid are expressed as percent of control value. After washing out phenylephrine and acetylcholine of the control contraction, β-amyloid augmented the phenylephrine induced contractions (P1). This effect was blocked by SOD. Washing out the phenylephrine and acetylcholine of the post peptide contraction and repeating the contractions caused further enhancement (P2). Values represent the mean ±SEM of nine or more experiments. The difference between control and P1 was significant for increasing doses of PE (p=NS, <0.005, <0.005, <0.001 respectively) and differences between β-amyloid treated and SOD plus β-amyloid treated were also significantly different with increasing doses of PE (p=NS, <0.005, <0.005, <0.001 respectively) indicating reduction of β-amyloid enhancement by SOD.

FIG. 12c shows that heat inactivated SOD, $H_2O_2$ inactivated SOD and the control protein albumin did not protect the blood vessel against the effects of β-amyloid, suggesting that the protective effects were not due to non-specific binding of β-amyloid by SOD.

Removing the SOD by rinsing restored the endothelial dysfunction in tissue pretreated with β-amyloid. This observation also argues against protection by SOD due to binding of β-amyloid, as both would be washed out during rinsing. Proteolytic destruction of β-amyloid by contaminants in the SOD preparation was excluded by the trace amounts (0.00014%) of protease (preparation from Alexis Corporation, San Diego, Calif.) in the SOD.

In order to elucidate the mechanism underlying these endothelial changes, various compounds known to affect the activity of oxygen radicals were examined. Under the conditions used, none of the compounds used (L-NMMA, indomethacin, SQ29548, or catalase) had any significant effect on the enhancement response as shown in FIG. 13.

Figure 13:
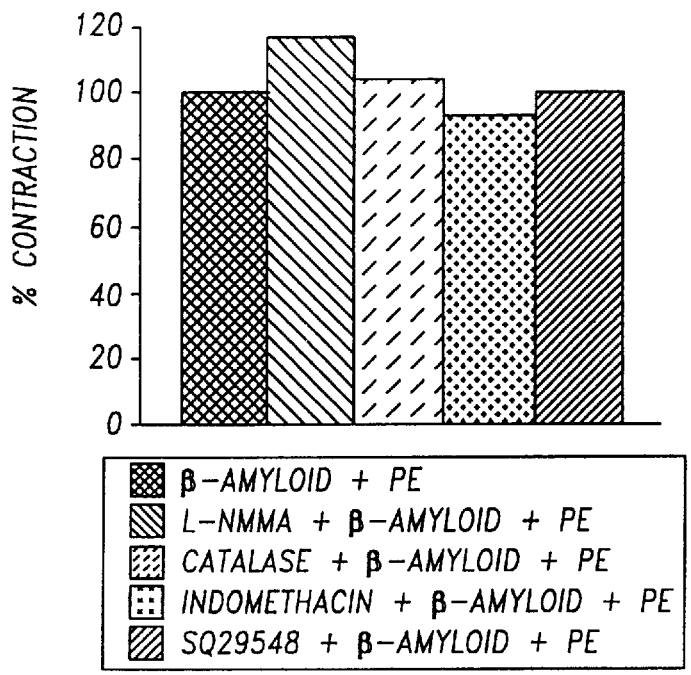
FIG. 13 is a histogram illustrating the effect of various drug treatments on β-amyloid augmentation of PE induced contractions.

As shown in FIG. 13, blood vessel rings were initially contracted with PE ($4\times10^{-8}$M). The tissue was then incubated for fifteen minutes with β-amyloid ($5\times10^{-7}$M) with or without the drug, followed by contractions with PE. The concentrations compounds used were: L-NMMA, an inhibitor of NO synthase ($10^{-4}$M); indomethacin, an inhibitor of the cyclooxygenase pathway ($10^{-5}$M); SQ 29548, a thromboxane $A_2$ receptor antagonist ($10^{-5}$M); and catalase (1000 units/ml). Values are represented as percentage of the maximal contraction obtained with β-amyloid and PE alone and standardized to remove the intrinsic effects (if any) of each drug on PE contraction alone. The results represent the mean ±SEM of five or more experiments. None of the compounds exerted any significant effect on the β-amyloid induced enhancement of PE mediated contraction.

Electron microscopic examination of the blood vessel ring treated under the same conditions (FIGS. 14A-F) showed endothelial damage after β-amyloid treatment which was prevented by pretreatment with SOD.

As shown in FIGS. 14A–F, blood vessel rings were incubated as previously described at 37° C. for thirty minutes either alone, or in presence of β-amyloid ($10^{-6}$M), or SOD (150 units/ml) and β-amyloid. The tissue samples were kept in glutaraldehyde solution at 4° C. until processed and then rinsed with cacodylate buffer. The tissues were post-fixed with 1% buffered osmium tetroxide, dehydrated with graded ethanol solutions, and embedded in a mixture of eponaraldite. Ultrathin sections were stained with uranyl acetate and lead citrate and viewed on model 7000 Hitachi transmission electron microscope. The inset bar indicates one micron. The experiment was repeated three or more times with blood vessels from different animals.

Incubation with β-amyloid induced significant damage to the endothelial cells with visible changes in the cell membrane, cytoplasm, nucleus and other organelles. Incubation periods of fifteen minutes and β-amyloid concentrations of $\geq 5\times10^{-7}$M were required to induce the morphological changes observed here. The endothelial damage induced by lower doses of amyloid also were blocked by s pretreatment with SOD (150 units/ml). The morphological changes are indicative of a necrotic process induced by β-amyloid.

The effects of β-amyloid peptide were examined on samples of rat coronary arteries prepared as described above. Referring specifically to FIG. 1, rat coronary arteries were treated with β-amyloid peptide ($A\beta_{40}$) causing constriction of the coronary arteries. The vasoconstrictor thromboxane $A_2$ (U46619,$10^{-7}$M also caused constriction of the blood vessel. Following treatment with the thromboxane $A_2$, the tissue was then rinsed, equilibrated with buffer, and treated with $10^{-6}$ MAβ for a period of fifteen minutes. The Aβ induced a small but detectable contraction in the rat coronary artery. The vasoconstriction induced by U46619 was significantly potentiated following treatment with Aβ.

A real time recording of rat coronary artery vasoactivity which was induced by β-amyloid peptides is shown in FIG. 2. The traces show the effect of $10^{-6}$M β-amyloid (A=$A\beta_{1-40}$ B=$A\beta_{25-35}$ C=$A\beta_{1-128}$. All of the fragments (A, B, C, induce constriction of the coronary artery. The $A\beta_{40}$ produce the longest sustained constriction. Following the constriction, there was a detectable relaxation of the coronary arteries.

FIG. 3 illustrates the effect of various amyloid fragments on the constriction of rat coronary arteries. Following control constriction with $10^{-7}$M U46619, the tissue samples were rinsed, equilibrated with buffer, and treated with $10^{-6}$M Aβ peptides for fifteen minutes. Following treatment with the Aβ peptides, the blood vessels were rinsed and again exposed to U46619. The values are expressed as percent of control constriction produced by U46619 alone.

The effect of increasing concentrations of amyloid β ($A\beta_{40}$) on rat coronary artery constriction induced by $10^{-7}$M U46619 is shown in FIG. 18. The blood vessel was treated with $10^{-9}$M to $10^{-6}$M concentrations of $A\beta_{40}$ for a period of fifteen minutes. The tissue was then rinsed and treated with U46619. Values are expressed as the increase in constriction relative to basal constriction with U46619 alone.

The action of the oxygen radical scavenging enzyme superoxide dismutase (SOD) on $10^{-6}$M $A\beta_{40}$ induced constriction of coronary arteries is shown in FIG. 19. SOD (150 units/ml) was added thirty seconds prior to the addition of Aβ. The last bar of the graph indicates the effect of rinsing the tissue to remove the SOD.

The effect of pretreatment of coronary arteries with a single dose ($10^{-6}$M) of $A\beta_{40}$ on acetylcholine induced relaxation is shown in FIG. 20. The blood vessel was preconstricted with $10^{-7}$M U46619 and relaxed with increasing doses of acetylcholine ($10^{-9}$M to $10^{-5}$M). As shown in FIG. 20, β-amyloid significantly reduced the vasodilation induced by acetylcholine.

The physiological effects of β-amyloid treatment on the coronary artery with and without pretreatment with SOD is shown in FIGS. 7A–C. FIGS. 7A–C are electron micrographs showing the endothelial cell layer in rat coronary artery. Blood vessel rings were incubated as previously described at 37° C. for thirty minutes either alone, or in the presence of β-amyloid ($10^{-7}$M) or SOD (150 units/ml) and β-amyloid. The tissue samples were kept in glutaraldehyde solution at 4° C. until processed and then rinsed with cacodylate buffer. The tissues were post-fixed with 1% buffered osmium tetroxide, dehydrated with grated ethanol solutions, and embedded in a mixture of eponaraldite. Ultra thin sections were stained with uranyl acetate and lead citrate and viewed on a model 7,000 Hitachi transmission electron microscope. The inset bar indicates two microns. The experiment was repeated three or more times with blood vessels from different animals. FIG. 7A is a control coronary artery and depicts normal endothelial cells closely adhering to the intimal elastic lamina lining of the lumen. FIG. 7B depicts a rat coronary artery treated with β-amyloid for thirty minutes at $10^{-6}$M. Derangement of the endothelial layer, condensed nucleus, separation from the intimal elastic lamina, and areas of denuded internal elastic lamina are evident following treatment with β-amyloid. FIG. 7C depicts a rat coronary artery pretreated with SOD (150 units/ml, for thirty seconds prior to the addition of β-amyloid). Intact endothelial cells are present having normal appearance and close adherence to the intimal elastic lamina.

FIGS. 15–21 illustrate the effects of β-amyloid alone or in combination with other agents on coronary artery tissue. These results are consistent with the results described above.

Experiments were also carried out to examine the effect of amyloid peptide on vascular tone and endothelial dysfunction in porcine coronary arteries. These experiments were carried out in order to show that the present invention elicits the same responses in animal tissue (porcine) which is very similar to human vascular systems.

The mechanism of action for diseases induced, at least in part, by β-amyloid induced free radical production resulting in endothelial destruction and vasoconstriction, can take anywhere from years to decades to manifest. The utility of the present invention in humans would therefore be difficult, if not impossible, to accumulate for the purposes of a patent as it would require testing over a extremely long period of time (as much as twenty-five years) using very low dosages of β-amyloid. For precisely this reason, the porcine model was utilized due to its similarities with the human vascular system. In the porcine experiments described below, larger doses of β-amyloid were administered over shorter periods of time in order to elicit and demonstrate the β-amyloid induced effects.

Figure 22:
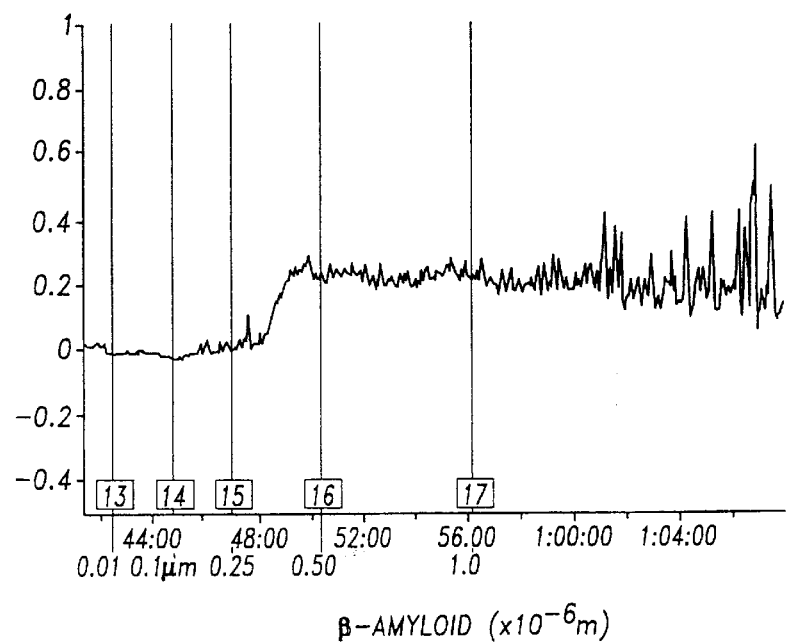

Freshly isolated porcine coronary arteries were studied by the methods described above for rat aorta. Referring to FIG. 22, adding increasing concentrations of amyloid peptide caused a dose dependent contraction of the porcine coronary artery samples. As shown in FIG. 22, at higher concentrations of amyloid peptide, there was a significant increase in activity.

The effect of pre-treatment with a single dose of amyloid protein on relaxation induced by increasing concentrations of the vasodilator bradykinin is shown in FIG. 23. Porcine aorta was preconstricted with a single dose of the vasoconstrictor U46619. Treatment of the aorta with amyloid peptide induced a significant increase in vasoconstriction and reduced the vasodilation caused by the bradykinin.

The results of the experiments illustrated in FIGS. 22 and 23 confirm the data set forth above for rat arterial tissue.

Amyloid β-peptides are central to the neuropathology of Alzheimer's disease (AD) [Glenner & Wong, 1984] but their precise role in the disease process remains in dispute. The neurotoxic properties of β-amyloid have been extensively investigated. Some researchers have detected neurotoxic effects while others failed to note such changes [Price, et al, 1992]. β-amyloid is also deposited in cerebral blood vessels in AD [Zeit, 1938] and abnormalities in microvasculature have been shown to precede other neuropathological features of AD [Buee, et al., 1994].

Expression of one or more copies of the ε4 allele of the apolipoprotein E gene confers increased risk for vascular degenerative disease [Davignon, et al., 1988] and also increases the risk for early expression of AD, although no vascular mechanisms have been identified which might explain the increased risk for AD. Bearing this in mind, those individuals expressing one or more copies of the ε4 allele of the apolipoprotein E may benefit from early intervention and treatment with antagonists of β-amyloid induced free radical excess production for example, superoxide anion modifiers, such as SOD.

The cytotoxic effects of oxygen radicals have been invoked as a major contributor to the pathology of neurodegenerative diseases such as AD. Much evidence points to the CNS microvasculature as the major target of free radical reactions, and the principal mediator of this damage is probably the superoxide radical [Kukreja, et al., 1986]. The endothelial dysfunction produced by β-amyloid seems to be initiated by the production of superoxide radicals. The superoxide radical can interact with NO to produce toxic peroxynitrite in a rapid reaction with a rate constant of $6.7 \times 10^9 M^1 s^{-1}$ [Huie & Padmaja, 1993]. This can lead to lipid peroxidation and account for the functional and morphologic damage to the endothelium. A damaged endothelium will exhibit enhanced vasoconstriction and diminished vasodilation due to impaired production of endothelium-derived relaxing factor (EDRF).

The β-amyloid mediated endothelial damage occurs at much lower concentrations than that used in previous studies (10–80 μM) showing effects like alteration of $Ca^{++}$ homeostasis or indirect toxicity [Mattson, et al., 1993], but similar to those showing direct trophic or toxic responses [Yankner, et al., 1990] or inhibition of potassium channels [Etcheberrigaray, et al., 1994]. However, in reports of neurotrophic and toxic effects of β-amyloid, incubation periods of two-four days using preaggregated β-amyloid are often required to demonstrate an effect. In the present study, the action of β-amyloid was demonstrated in less than one minute without the need for pre-aggregation, suggesting a novel and possibly physiologically relevant effect. In addition the biological response was demonstrated in intact tissue with viable permeability barrier and cell to cell interaction.

A number of endothelial enzymes (xanthine oxidase, lipooxygenase, prostaglandin hydroperoxidase [Furchgott, et al., 1992], nitric oxide synthase [Pou, et al., 1992]), and NADPH dependent oxido-reductase are known to produce superoxide radicals. The current study provides no evidence as to the precise pathways involved in the production of superoxide by β-amyloid. Even though the action of β-amyloid delineated herein on a peripheral blood vessel, such an effect on brain vasculature is likely.

Vasogenic brain edema is the most common brain edema following brain ischemia and injury. Characteristic features of this edema are increased permeability of brain capillary endothelial cells to macromolecules, increased extracellular space and brain fluid content. Although the underlying causes of vasogenic edema are unknown, the central feature of this condition is alterations in the structural and functional integrity of brain endothelial cells [Acta Neurochirurgica, 1993, 57:64–72; Brain and nerve 1994, 46:1155–61]. Applicant's assert that β-amyloid induced oxygen radicals, particularly superoxide radicals are involved in the perturbation of the structural and functional integrity of the endothelial cells. Applicants further assert that β-amyloid antagonists, compounds that decrease the production of β-amyloid, oxygen radical scavengers including SOD mimicking compounds and antioxidants will be effective in the treatment of brain edema by protecting the integrity of the endothelial cells.

Effect of β-amyloid on Bovine Cerebral Artery.

Freshly dissected bovine mid cerebral arteries were cut into 3 mm rings and studied in tissue chamber as described earlier. Contraction of the blood vessel to the vasoconstrictor U46619 was studied before and after treatment with 1 $\mu$M β-amyloid for 15 minutes. The contraction induced by the vasoconstrictor was significantly increased by amyloid. The vasodilatory effect of bradykinin was markedly reduced by β-amyloid. (See FIG. 24).

If brain or platelet derived β-amyloid were to come into contact with the endothelium, the free radical production could induce local damage and reduce local blood flow, further increasing oxidative stress and upregulating neuronal β-amyloid production [Tomimoto, et al., 1994]. Other factors which effect the local oxidative stress on cerebral vasculature would influence this process.

Endothelial damage is currently recognized as an early event in the development of vascular disease [Gimbrone, et al., 1995]. The β-amyloid mediated free radical production and subsequent endothelial damage may have relevance in head injury and cerebrovascular disease and may play a central role in the Alzheimer disease process.

These findings show a physiologic role for β-amyloid. The physiologic roles play a first step in the development of diagnostic and therapeutic protocols outlined below.

β-amyloid may have a normal physiologic role in mediating vasoactivity. This may be particularly relevant under certain situations such as conditions of tissue damage. There is some evidence suggesting that parts of the β-amyloid precursor protein molecule are involved in the acute phase response, and that β-amyloid has a role to play in the activation of other acute phase reactants. The generation of superoxide is likely to have a plethora of secondary effects; some of these effects mediated via their effects on nitric oxide (NO) and others mediated via other systems. β-amyloid may serve to regulate the role of nitric oxide, again perhaps this may be important during the inflammatory response or other conditions of tissue damage. Although NO acts as a physiologic messenger in normal circumstances it can also be toxic. Regulation of the levels of this messenger would be essential for cell longevity and may be attained by a number of mechanisms. Neurons are particularly prone to generate NO, having high levels of NOS. There may be other circumstances in which the regulation of NO activity might be particularly important. One mechanism which is essentially dependent on No production is the long term excitation of neurons in the process of memory.

Figure 9:
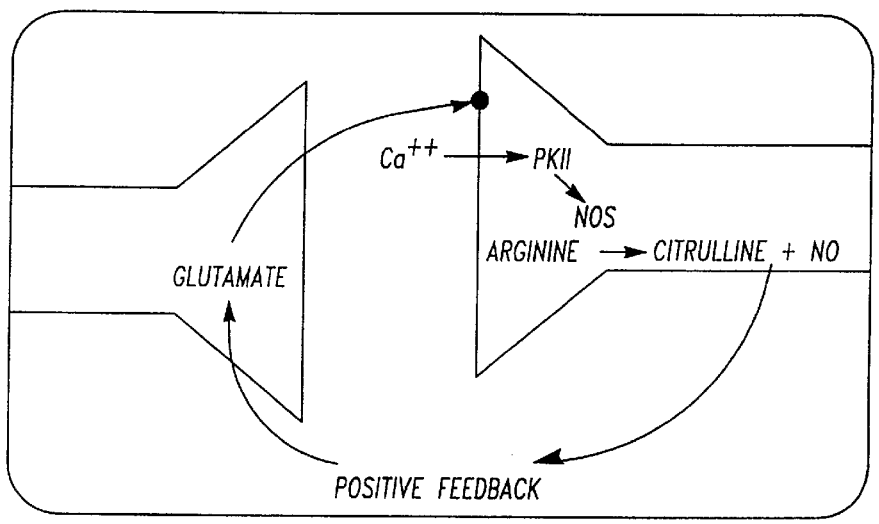
FIG. 9 shows glutamate as an excitatory amino acid which stimulates the influx of calcium ions post synaptically via the NMDA receptor, Calcium/calmodulin dependent activation of protein kinase II allows phosphorylation of nitric oxide synthase catalyses the production of nitric oxide.

The hippocampal formation has long been implicated as integral in the formation of memories and in the process of learning. Long Term Potentiation (LTP, FIG. 9) is the mechanism by which a neuron "remembers" that it has received synaptic contact before and it may also be the mechanism by which memory is maintained.

The data herein suggests that one of the physiologic roles of β-amyloid is to protect against an excitotoxic cascade which is a result of increasing intracellular calcium levels, but stimulated by NO positive feedback. Production of β-amyloid at synaptic terminal is enhanced as these are the sites of neuronal plasticity in which it has been suggested β-APP plays a significant role. Certainly βAPP is known to be particularly abundant at the neuronal synapse. This would make it ideally positioned to regulate the NO message passing between adjacent cells. It has been recently proposed that the site of production of the NO associated with LTP is the endothelium rather than the neurons. The effects of superoxide production of endothelial cells after stimulation with β-amyloid might therefore have immediate effects on LTP. Continued and prolonged stimulation of neurons by superoxide produced in endothelial cells might cause permanent cell damage.

In addition, it can be proposed that those cells where NO message was being destroyed might show up-regulation of NOS. In the neurodegenerative condition, Alzheimer's disease, it has been shown that the NOS expressing neurons are indeed spared suggesting the toxic effects of NO are being moderated. The removal of superoxide in this process will also inhibit the destructive properties of this radical. Thus, β-amyloids show neuroprotective properties. Such properties have been previously noted [Hyman et al., 1992].

However, the findings herein suggest that β-amyloid could produce neurotoxicity by the generation of superoxide. In those cells where the superoxide radical cannot be absorbed by high levels of nitric oxide or similar species, the presence of superoxide may have deleterious effects, leading to an increase intracellular calcium levels in smooth muscle cells and also in endothelial cells. β-amyloid has been shown to cause increased intracellular calcium levels when applied to neurons and fibroblasts. It is proposed that one of the mechanisms by which this occurs is via free radical production.

The implication that β-amyloid can stimulate endothelium and perhaps other cells to produce superoxide would therefore be important in the pathogenesis of Alzheimer's disease. In particular, the generation of superoxide and other free radicals having deleterious effects contributes to Alzheimer's disease pathogenesis.

β-amyloid has long been implicated in Alzheimer's disease. Deposition of β-amyloid in the brain of all cases of Alzheimer's disease is required for neuropathologic diagnosis although the significance of β-amyloid deposition has been in dispute. More recently, largely due to the normal occurrence of βAPP metabolites in CSF, it has been proposed that βAPP may have one or more physiologic roles.

One mechanism through which β-amyloid may facilitate the pathogenesis of Alzheimer's disease involves the free radical/oxidative damage as the disease's primary pathogenic mechanism. An ever-increasing body of experimental evidence is establishing free radical/oxidative damage as a major factor in general brain aging and a determinant in Alzheimer's disease pathogenesis [Harman, 1993]. Evidence consistent with a major role of free radicals and oxidative damage in the pathogenesis of Alzheimer's disease should be considered. First, iron (which catalyzes hydroxyl free radical formation) accumulates in both neuritic plaques and neurofibrillary tangles. Moreover, iron levels are elevated in cognitively-important regions of Alzheimer's disease brains such as the neocortex, hippocampus, and nucleus basalis. Head injury with brain trauma is a known risk factor for Alzheimer's disease, and may result in the release of free iron from RBC's and the formation of free radicals. Additionally, enhanced lipid peroxidation is present in the neocortex of Alzheimer's disease brains--a finding indicative of increased free radical-induced damage to cell membranes. Perhaps relatedly, some studies report increased lipofuscin (the end product of lipid peroxidation) in various areas of Alzheimer's disease brains, while others report increased lipofuscin selectively in neurofibrillary tangle-containing neurons. In view of the fact that mitochondrial DNA is particularly sensitive to free radical-induced damage, it is noteworthy that Complex IV (cytochrome oxidase) of the electron transport system is reduced in the hippocampus of Alzheimer's disease brains. There is, therefore, reason to postulate that a facilitatory relationship exists in Alzheimer's disease pathogenesis between free radical/oxidative damage and Aβ neurotoxicity. We propose that the mechanism of β-amyloid stimulation of superoxide production is the mediating link in this relationship.

The exact cause underlying vasospasm in several clinical situations is unknown. For instance, the cause of the often prolonged cerebral vasospasm following head injury is unknown. This vasoactivity can often severely hinder supportive measures and may in itself be life threatening leading, as it does, to poor cerebral perfusion. Interestingly, one molecule which shows increased genetic expression and deposition in the time immediately after head injury is βAPP, the parent molecule of Aβ. Accordingly, increased Aβ release might contribute to head injured vasospasm via the mechanism observed herein. Blockage of the β-amyloid response would have beneficial effects in this instance.

Other Implications of the Effects of the Generation of Superoxide by β-amyloid

Using the above-described information, a test for Alzheimer's disease based on peripheral blood flow measurements is disclosed. The test includes measuring initial peripheral blood flow and then administering a vasodilator. Based on experimental data, herein, there will be a tendency toward peripheral vasoconstriction and therefore, a peripheral vasodilator will have less effect in Alzheimer's disease cases than in non-Alzheimer's disease cases. The test for Alzheimer's disease based on these differences is as follows. The peripheral blood flow can be measured and the response to acetylcholine and is quantitated as described by Gilligan et al. [1994]. The basal blood flow is determined three minutes following intra-arterial infusion of acetylcholine chloride (Sigma Chemical Co.) at 7.5 mg/min. to 20 mg/min. Acetylcholine is infused for five minutes and forearm blood flow is measured in the last two minutes of infusion. The vascular resistance will be greater in subjects with Alzheimer's disease as compared to matched controls. The oxygen level in these subjects is simultaneously monitored using a pulse oximeter to measure the color of the blood as an indicator of peripheral blood oxygen concentration.

Data exists showing that there is reduced peripheral blood flow in patients with AD, however, no mechanism or explanation was provided [Winblad et al. 1994].

It is possible that β-amyloid or smaller active peptide fragments contribute to the pathophysiology of Alzheimer's disease and other degenerative diseases by the generation of a relative excess of superoxide or via the vasoactive properties of β-amyloid. This direct effect on the blood vessel and the resulting changes in blood flow affect biological processes long before neuropathological changes are observed in degenerative diseases. By its ability to reduce effective nitric oxide levels, β-amyloid affects a number of important biological functions including long-term potentiation and memory. The superoxide radicals induced by β-amyloids interact with β-amyloid and other proteins to generate aggregates eventually leading to the plaques characteristic of Alzheimer's disease. The use of compounds to alter the interaction of β-amyloid with blood vessels are a significant advance in the treatment of degenerative diseases as discussed above.

The Relevance of the present disclosure to other research in AD

Applicants' findings disclosed herein suggest that endothelial dysfunction may contribute directly to neuronal death. There is existing evidence that AD has a significant vascular component. Research from several fields: epidemiology, pathological studies (pre- and post-disease onset), genetic findings (HCHWA-D) and the examination of other known risk factors (APOE) contribute to this concept. Although it is clear that the generally accepted current understanding of AD pathology does not include a significant vascular component a re-examination of the current literature in these fields is warranted.

Epidemiologic studies suggest risk factors and protective factors for AD. Estrogens and non-steroidal anti-inflammatory agents and nicotine (smoking) have been suggested as protective against the disease. Estrogens are known to be protective in other arterial disease such as coronary artery disease and are a suggested prophylactic treatment of coronary vessel disease in humans. Non-steroidal anti-inflammatory agents are known to inhibit cyclo-oxygenase, a known producer of superoxide anions, which is pertinent to this application and via this and other mechanisms probably provide non-specific anti-inflammatory protection to vessels. Platelet aggregation is suppressed by NSAIs and for this reason is a preferred treatment for the prevention of stroke. It is feasible that the protection provided by both estrogens and NSAIs in vascular disease is also protective in AD. The vascular effects of nicotine are noteworthy as smoking has been reported as negatively correlated with the disease in several studies. Nicotinic receptors in the cerebrovascular circulation respond to nicotine by vasodilation.

Several studies show that "cognition" can be improved by influencing risks for vascular disease. Studies have shown that improvement in cognitive function can occur as a result of modification of factors known to be risks for peripheral and cerebral vascular damage. Reduction of blood pressure, for instance, results in improvement in cognition for dementia cases.

Reduced cerebral blood flow is well recognized in AD although it is generally believed that reduced cerebral blood flow is a consequence of the disease rather than a cause. In particular, reduced oxygen and metabolic requirements of degenerating neurons are thought to signal for less local oxygen supply by adjacent vessels. Cerebral hypoperfusion may be a contributory factor in AD as suggested by at least one study. Consistently, several studies have shown that in other conditions, and perhaps in AD, increasing cerebral perfusion is correlated with decreasing memory problems. One of the key questions that arises from this work concerns the relationship between blood flow and the disease process in AD. Traditional thinking has it that as the AD process progresses, neuronal demand on nutrients including oxygen falls leading to reduced blood flow. However, at least one study shows that symptomatology and reduced blood flow occur simultaneously in AD. It is well recognized that the first signs of AD may be reduced cerebral metabolism as measured by PET scanning. The measurements of glucose and oxygen uptake in such scans is dependent upon cerebral blood flow and, therefore, suggests that some of the observed decreases in cerebral blood flow measurements may be due to abnormalities in the cerebral microvasculature.

Peripheral blood pressure is lower in AD cases in several studies possibly suggesting that cerebral pressure may be increased or that there may be hypoperfusion as a result of reduced peripheral resistance. Other abnormalities have been noted in the cardiovascular responses of AD patients—which is generally attributed to autonomic nervous system dysfunction. During rest, AD patients have lower mean systolic and diastolic blood pressure but the same heart rate as control patients. After tilting, AD patients have a greater increase in heart rate, and the mean systolic blood pressure falls significantly (126 mmHg compared with 160 mmHg in controls (p less than 0.001) in one study [Elmstahl et al., 1992].

This effect seems specific to AD as noted in blood pressure (BP) measurements in a variety of dementias: Mean blood pressure and fasting blood glucose levels were lower in patients with AD, 94+/−12 mmHg and 4.3+/−0.5 mmol 1-1, compared to patients with unspecified dementia (NUD), 100+/−10 mmHg and 5.5+/−2.5 mmol 1-1 (P<0.05) and vascular dementia (VaD), 114+/−12 mmHg and 5.6+/−1.6 mmol 1-1 (P<0.001) and the age-matched controls. Furthermore, the severity of BP abnormalities in AD may progress with the disease: AD patients in a study by Wang et al., (1994) had a lower systolic blood pressure than controls in both supine (130.7+/−17.4 vs. 145.4+/−20.7 mmHg, p<0.02) and standing (129.2+/−20.1 vs. 146.6+/−21.1 mmHg, p<0.008) positions, a difference which was especially noted in those patients with more severe dementia. This seems corroborated by other groups: Burke et al., (1994) showed that although BP measurements were significantly decreased by between 6.9% to 15.9% in AD patients, sustained BP declines started in the third to fourth year after diagnosis. One explanation for these findings might be that there is a peripheral lowering of BP in response to central abnormalities. Applicants' data suggests that the AD patient might suffer from local abnormalities in cerebral microvascular flow. One scenario which explains the abnormalities in peripheral blood pressure and the finding of central hypoperfusion, is that amyloid interacts with small blood vessels (arterioles, precapillaries) and causes vasoconstriction in the manner described above. Beyond the constricted vessels there can be a resultant hypoperfusion to the supplied tissue. The peripheral resistance could be increased due to the constricted vessels and a homeostatic lowering of peripheral blood pressure would result.

There is evidence that there is regional reduced cerebral blood flow in AD and that it is associated with small vessel damage in AD. White matter magnetic resonance hyperintensities are seen on MRI scanning in dementia of the Alzheimer type and are thought to represent damage to neuronal tissue as due to small cerebral vessel pathology (Waldemar et al., 1994). In a prospective MRI study the presence, appearance, volume, and regional cerebral blood flow (rCBF) correlates of periventricular hyperintensities (PVHs) and deep white matter hyperintensities (DWMHs) were examined in 18 patients with probable Alzheimer's disease and in ten age matched healthy control subjects, all without major cerebrovascular risk factors. It was concluded that DWMH lesions may be associated with reduced rCBF in the hippocampal region. A further study has suggested that cerebral hypoperfusion may contribute to the genesis of white matter lesions in AD cases [Blenow et al., 1991].

One of the main themes of current treatment in AD is the use of anticholinesterases. The original rational for the use of antichiolinesterase therapies was that there is a deficiency of acetylcholine in the cortex in AD. This neuroteransmitter is known to mediate learning and memory however it is also responsible for vasodilation in the arterial vasculature. Thus, consistent with the beneficial effects of anticholinesterases seen in some AD patients, there may be a central vasodilatory effect, overcoming the vasoconstriction which applicants suggest may be important in disease etiology. It has been suggested that there may be a BP related response to treatment with anticholinesterases. In one study pretreatment BP drop predicts poor response to anticholinesterase treatment in AD. Non responders demonstrated significantly greater decreases in pretreatment systolic postural BPs when going from a supine to sitting position than did responders [Pomara et al., 1991]. In a second study asking the question "Do blood pressure and age predict response to tacrine (THA) in Alzheimer's disease?" researchers found that the magnitude of PSOP fall and increasing age each contributed to the prediction of response to tacrine [Schneider et al., 1991].

An important finding for risk for AD is the association between the APOE $\epsilon$4 locus and AD. This relationship has been confirmed and replicated in over 30 independent studies. One key question in the light of the present discussion is the relationship of APOE locus to vascular disease. By virtue of it's known risk for vascular damage, APOE could enhance damage caused by amyloid in the cerebral microvasculature. In this regard the association found between $\epsilon$4 and the amount of amyloid angiopathy is pertinent. Cerebral amyloid angiopathy (CAA) is characterized by cerebrovascular deposition of the amyloid beta-peptide, leading to intracerebral hemorrhage in severe cases. An increase in $\epsilon$4 allele frequency (0.54+/−0.07) was observed in AD cases with amyloid angiopathy, compared to those who did not have amyloid angiopathy (0.36+/−0.04). Contrary to reports suggesting an association of $\epsilon$4 and atherosclerosis, the $\epsilon$4 allele frequency was similar in cases with or without concurrent brain infarcts suggesting the brain infarcts aren't causing the dementia but that other vessel related pathogenic pathways are involved [Zubenko et al., 1994]. Researchers concluded that ApoE $\epsilon$4 is a risk factor for CAA and CAA-related hemorrhage, independent of its association with Alzheimer's disease [Greenberg et al., 1995]. This would support the notion that APOE $\epsilon$4 is an independent risk factor cerebral angiopathy rather than Alzheimer's disease per se. Applicants would contend that the known risk for vascular disease conferred by the APOE $\epsilon$4 allele is operative in AD and that in conjunction with amyloid vaso-activity and free radical mediated damage $\epsilon$4 hetero- or homo-zygotes develop AD earlier that non $\epsilon$4 carriers.

The 64 of the apolipoprotein E (APOE) gene has been shown to be associated with the more common, late-onset, form of AD [Strittmatter et al., 1993a; Corder et al., 1993; Saunders et al., 1993]. The APOE locus appears to influence the rate of progression of the disease, but is not in itself causative [Bennett et al., 1995]. Apolipoprotein E binds to low density lipoprotein (LDL) receptors and regulates lipoprotein metabolism. The $\epsilon$4 allele is a recognized risk factor for hypocholesterolaemia and atherosclerosis [Davignon et al., 1988], but as Alzheimer's disease is excluded as a diagnosis in any dementia patients demonstrating gross vascular disease, hypotheses on the nature of ApoE's involvement in the AD process have focused not on it's known atherogenic effects, but rather on it's potential interaction with the βAPP molecule [Strittmatter et al., 1993b] or it's effects on neuronal plasticity and regeneration [Nathan et al., 1994] suggesting a role for ApoE in neuronal maintenance and outgrowth, and in the regeneration of neurons after injury.

Lessons from Genetic lesions

Previous studies of genetic lesions in the β-APP molecule (the precursor of β-amyloid discussed throughout this disclosure) have noted that phenotypes may be largely associated with cerebral vascular disease and not AD. For instance a mutation within the β-amyloid sequence of β-APP which causes Hereditary Cerebral Hemorrhages with Amyloidosis-Dutch type (HCHWA-D) presents as a series of hemorrhages to individuals in their forties, fifties and sixties. Examination of the verebral vasculature in these cases reveals revealed evidence of multiple hemorrhagic events with deposits of β-amyloid in vessels and vessel tortuosity.

These cases have previously been considered as a model for amyloid (congophilic) plaque formation [Matt-Schieman et al., 1994] because if affected individuals reach a significant age (i.e. do not die from early hemorrhage) they develop congophilic plaque. This sequence of events of damaged blood vessels and then plaque formation might suggest a similar sequence in the related condition of Alzheimer's disease.

In those cases of early onset AD caused by mutations in β-APP, extensive β-amyloid deposition with congophilic angiopathy and widespread senile plaques can occur. [Rossor et al., 1993].

From a neuropathological perspective, cerebral amyloid angiopathy (CAA) is a common occurrence in AD with some estimates suggesting 100% of cases are affected. Typically amyloid fibrils are found in the vascular basement membrane and these lesions in the microvasculature are often associated with large deposits of amyloid surrounding the vessels and sometimes occluding their lumen. However, until now it has not been clear that β-amyloid is directly toxic to structures in the physiologically active vessel wall. Interestingly the premorbid pathology in humans, Down's syndrome cases and transgenic mice all suggest the cerebrovasculature as a key site of action of β-amyloid. A transgenic animal expressing a gene promoting the carboxyl-terminal 100-amino acids of β-APP resulted in a pathology showing accumulations of β-amyloid in the cerebrovasculature.

Taken together these observations can be explained by the central role of the cerebrovasculature in the pathogenesis of AD as suggested above by applicants.

The evidence presented here unifies that observations in Alzheimer's disease regarding a central role for β-amyloid and suggests a prominent role for β-amyloid in the aging process as well as degenerative diseases in general. The model is consistent with slow onset of Alzheimer's disease and a mechanism for the observed memory deficits long before the neuropathological changes are detected. Young individuals have higher antioxidant capacity and can withstand free radical stress. Aging, in conjunction with environmental factors or genetic defects including increased β-amyloid production, by depleting antioxidant levels can exacerbate the effects of free radicals induced by β-amyloids. The long term oxidative stress induced by β-amyloids, along with the decreased production of nitric oxide and significant effect on the blood vessel tone and, thus blood flow, could play an important role in the susceptibility to, and the progression of degenerative diseases.

Applicants data demonstrate a cascade or mechanism by which Aβ can be all or in part a cause of diseases inducing an excess free radical production and resulting in endothelial destruction and vasoconstriction. In general, Aβ induces vascular (vessel) constriction causing a lack of both oxygen and nutrient perfusion of the surrounding vascular tissue. This lack of both oxygen and nutrient perfusion leads to oxidative stress in the surrounding tissues and is mediated via the generation of excess free radicals, and can cause irreversible endothelial cell death.

A method for prophylactic treatment of individuals possessing AD risk factors including age or genetic aberrations listed above by administering a modifier of superoxide anion formation or β-amyloid antagonist is disclosed.

In view of the above, there have been developed protocols for utilizing the present invention for diagnostic and therapeutic purposes.

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

TABLE I

| PE $(\times 10^{-8}$ M) | control (±SEM) | +β-Amyloid P1 (±SEM) | +β-Amyloid P2 (±SEM) | +β-Amyloid +SOD ±SEM) |
|---|---|---|---|---|
| 2 | 18 (8.0) | 13.3 (5.9) | 20 (5.0) | 12 (5.7) |
| 4 | 65 (5.8) | 75 (6.0) | 99 (15.0) | 62 (11.0) |
| 8 | 86 (4.0) | 105 (15.0) | 133 (20.0) | 93 (13.0) |
| 16 | 100 | 128 (11.7) | 141 (17.6) | 110 (11.0) |

REFERENCES CITED

Beckman et al., "ALS, SOD and peroxynitrite" *Nature*, 364:584 (1993).

Bennett, C. et al., "Evidence that the APOE locus influences rate of disease progression in late onset familial Alzheimer's disease but is not causative", *Neuropsych.Genet.* 60:1–6 (1995).

Betz et al., *Basic Neurochem.* Molecular Cell, (Raven Press Ltd., NY) 5th Ed., pp.681–699.

Betz, "Oxygen Free Radicals and the Brain Microvasculature" *The Blood-Brain Barrier*, edited by William M. Pardridge, Raven Press, Ltd. New York, pp. 303–321.

Blenow, K. et al., "White-matter lesions on CT in Alzheimer patients: relation to clinical symptomatology and vascular factors", *Acta Neurologica Scandinavica* 83(3):187–93.

Brem et al., "Polymers as controlled drug delivery devised for the treatment of malignant brain tumors" *Eur. J. Pharm Bio. Pharm,* 39: pp. 2–7 (1993).

Bulkley G. B. *Surgery,* 113:479–483 (1993).

Buee et al., "Pathological alterations of the cerebral microvasculature in alzheimer's disease and related dementing disorders" *Acta Neuropathol.* 87:469–480 (1994).

Burke, W. et al., "Blood pressure regulation in Alzheimer's disease", *Journal of the Autonomic Nervous System* 48(1) 65–71 (1994).

Burke and Olson, "Preparation of Clone Libraries in Yeast Artificial-Chromosome Vectors" in *Methods in Enzymology*, Vol 194, "Guide to Yeast Genetics and Molecular Biology", eds. C. Guthrie and G. Fink, Academic Press, Inc. Chap. 17, pp. 251–270 (1991).

Byung Paul Yu, "Cellular defenses against damage from reactive oxygen species" *Physiological Review* 74:139–162 (1994).

Capecchi, "Altering the genome by homologous recombination' *Science* 244:1288–1292 (1989).

Corder, E. et al., "Gene dose of apolipoprotein E type 4 allel and the risk of Alzheimer's disease in late onset familes", *Science* 261:921–923 (1993).

Davies et al., "Targeted alterations in yeast artificial chromosomes for inter-species gene transfer", *Nucleic Acids Research*, Vol. 20, No. 11, pg. 2693–2698 (1992).

Davignon et al., *Atherosclerosis* 8: 1–21 (1988).

Dickinson et al., "High frequency gene targeting using insertional vectors", *Human Molecular Genetics*, Vol. 2, No. 8, pp. 1299–1302 (1993).

Elmstahl, S. et al., "Autonomic cardiovascular responses to tilting in patients with Alzheimer's disease and in healthy elderly women", *Age and Aging* 21(4):301–7 (1992).

Etcheberrigaray et al., "Soluble β-Amyloid Induction of Alzheimer's Phenotype for Human Fibroblast K+ Channel", *Science* 264: 276–279 (1994)

Furchgott and Zawadzki, "Obligatory role of endothelial cells in the relaxation of arterial smooth muscle by acetylcholine" *Nature* 288:373–376 (1980).

Furchgott et al., *Jap. J. Pharmacol.* 58: Supp.2, 185–191 (1992).

Gilligan et al., "Acute vascular effects of estrogen in postmenopausal women" *Circulation* 90:786–791 (1994).

Gimbrone et al., Ann. New York Acad of Sci. 148: 122–131 (1995).

Glenner and Wong, "Alzheimer's disease and Down's syndrome: Sharing of a unique cerebrovascular amyloid fibril protein" *Biochem. Biophys. Res. Commun.* 122:1131–1135 (1984).

Glenner and Wong, "Alzeheimers' disease: Initial report of the purification and characterization of a novel cerebrovascular amyloid protein" *Biochem. Biophys. Res. Commun.* 120:885–890 (1984).

Greenberg, S. et al., "Apolipoprotein E epsilon 4 and cerebral hemmorrhage associated with amyloid angiopathy", *Annals of Neurology* 38(2):254–9 (1995).

Hall, E. D. *Annals of Emergency Medicine* 22:1022–1027 (1993).

Halliwell, B. "Superoxide, iron, vascular endothelium and reperfusion injury" *Free Radical Re-Commun.* 5:315–8 (1989).

Harman, "Free radical theory of aging: Role of free radicals in the origination and evolution of life, aging, and disease processes, in *Free Radicals. Aging and Degenerative Diseases*, edited by Johnson, Jr. J. E., Walford, R., Harman, D., and Miquel, J., New York, Alan R. Liss, pp. 349 (1986).

Harman, "Free Radical Theory of Aging: a Hypothesis on Pathogenesis of Senile Dementia of the Alzheimer's Type" *Age*, 16:23–30 (1993).

Hirosumi, *BBRC* 152: 301–307 (1988)

Huie and Padmaja, S. *Free Radicals Res. Comm.* 18: 195–199 (1993).

Huxley et al., "The human HPRT gene on a yeast artificial chromosome is functional when transferred to mouse cells by cell fusion", *Genomics*, 9:742–750 (1991). Hyman et al., "Nitric Oxide Synthase-Containing Neurons in the Hippocarnpal Formation in Alzheimer's Disease" *Ann. Neurol.* 32:818–820 (1992).

Jakobovits et al., "Germ-line transmission and expression of a human-derived yeast artificial chromosome", *Nature*, Vol. 362, pp. 255–261 (1993).

Katusic and Vanhoutte, "Superoxide anion is an endothelium-derived contracting factor" *Am. J. Physiol.* 257:H33–7 (1989).

Kontos et al., "Oxygen radicals mediate the cerebral arteriolar dilation from arachidonate and bradykinin in cats" *Circ. Res.* 55:295–303 (1984).

Kukreja et al., *Circ, Res.* 59: 612–619 (1986).

Lamb et al., "Introduction and expression of the 400 kilobase precursor amyloid protein gene in transgenic mice", *Nature Genetics*, Vol. 5, pp. 22–29 (1993).

Lipton et al., "A redox-based mechanism for the neuroprotective and neuordestructive effects of nitric oxide and related nitroso-compounds" *Nature* 364:626–632 (1993).

Mandybur T. I., *Neurology* 25, 120–126 (1975).

Marshall et al., "Independent blockade of cerebral vasodilation from acetyl-choline and nitric oxide" *Am. J. Physiol.* 255:H847–54 (1988).

Mattson et al., *TINS* 16: 409–414 (1993).

Matt-Schieman M. et al, "Hereditary cerebral hemorrhage with amyloidosis (Dutch): a model for congophilic plaque formation without neurofibrillary pathology", *Acta Neuropathologica* 88(4) :371–8 (1994).

Moncada et al., "Endothelium-de rived relaxing factor: identification as nitric oxide and role in the control of vascular tone and platelet function" *Biochem Pharmacol.* 37:2495–2501 (1988).

Nathan, B. et al. "Differential Effects of Apolipoproteins E3 and E4 on Neuronal Growth in Vitro" *Science* 264:850–852 (1994).

Offernann, M. et al., "Antioxidants and Atherosclerosis: a molecular perspective", *Heart Disease and Stroke* 3:52–57 (1994).

Olanow, C. W., "A radical hypothesis for neuro degeneration", *TINS*, 16:439–444 (1993).

Pardridge et al., *West J. Med.* 156(3) 281–286 (1992).

Pardridge et al., *Pharm. Toxicol.* 71(1);3–10 (1992).

Pardridge et al., *Proc. Natl. Acad. Sci. USA* 90(7) 2618–2622 (1993).

Pomara, N. et al., "Pretreatment postural blood pressure drop as a possible predictor of response to the cholinesterase inhibitor velnacrine (HP 029) in Alzheimer's disease" *Psychopharmacology Bulletin* 27(3) :301–7 (1991).

Pou et al., "Generation of Superoxide by Purified Brain Nitric Oxide Synthase" *J. Biological Chem.* 267, 34:24173–6 (1992).

Price et al., *Neurobiology of Aging* 13, 623–627 (1992).

Rosenblum, "Effects of free radical generation on mouse pial arterioles: probable role of hydroxyl radicals" *Am. J. Physiol.* 245:H 139–42 (1983).

Rosenblum, "Hydroxyl radical mediates the endothelium-dependent relaxation produced by bradykinin in mouse cerebral arterioles" *Circ. Res.* 61:601–3 (1987).

Rosser, M. et al., "Alzheimer's disease families with amyloid precursor protein mutations" *Annals of the New York Academy of Sciences* 24:695:198–202 (1993).

Rothstein, "Targeting, disruption, replacement, and allele rescue: integrative DNA transformation in yeast" in *Methods in Enzymology*, eds C. Guthrie & G. Fink, Academic Press, Inc. Vol 194, "Guide to Yeast Genetics and Molecular Biology", Chap. 19, pp. 281–301 (1991).

Saunders, A. et al., "Association of Apolipoprotein E allele E4 with late onset familial and sporadic Alzheimer's disease" *Neurology* 43: (1993).

Savita, Prashar et al., "Antioxident enzymes in RBC as a biological index of age related vascular degeneration", *Acta Ophthalmologica* 71:214–218 (1993).

Schedl et al., "A yeast artificial chromosome covering the tyrosinase gene confers copy number-dependent expression in transgenic mice", *Nature*, Vol. 362, pp. 258–261 (1993).

Schneider, L. et al., "Do blood pressure and age predict response to tacrine (THA) in Alzheimer's disease", *Psychopharmacology Bulletin* 27(3):309–14 (1991).

Scholz W., *Zeit. Neurol. Psychiat.* 162, 694–715 (1938).

Sneddon and Vane, "Endothelium-derived relaxing factor reduces platelet adhesion to bovine endothelial cells" *Proc. Natl. Acad. Sci. USA* 85:2800–4 (1988).

Strauss et al., "Germ line transmission of a yeast artificial chromosome spanning the murine $\alpha_1$ (I) collagen locus", *Science*, Vol. 259, pp. 1904–1907 (1993).

Strittmatter, D. et al., "Apolipoprotein E: High-avidity binding to β-amyloid and increased frequency of type 4 allele in late-onset familial Alzheimer disease", *Proc. Natl. Acad. Sci. U.S.A.* 90: (1993a)

Strittmatter, D. et al., "Binding of hum an apolipoprotein E to synthetic amyloid beta peptide: isoform-specific effects and implications for late-onset Alzheimer's disease", *Proceedings of the National Academy of Sciences of the United States of America* 1:90(17):8098–102 (1993b).

Teller, Jan K. et al. *Natase Medicine* 2:93–95 (1995).

Thomas et al, "β-amyloid-mediated vasoactivity and vascular endothelial damage" *Nature* (In Press)

Tomimoto et al., *J. Cereb Blood Flow Metab* 14(4): 565–73 (1994).

Vinters H. V., *Stroke* 18, 311–324 (1987).

Waldema, G. et al., "White matter magnetic resonance hyperintensities in dementia of the Alzheimer type: morphological and regional cerebral blood flow correlates", *Journal of Neurology, Neurosurgery & Psychiatry* 57(12) :1458–65 (1994).

Wang, S. et al., "Cardiovascular autonomic functions in Alzheimer's disease", *Age & Aging*, 23(5) :400–4 (1994).

Wei et al., "Superoxide generation and reversal of acetylcholine-induced cerebral arteriolar dilation after acute hypertension" *Circ. Res.* 57:781–7 (1985).

Yankner et al., *Science* 250: 279–282 (1990).

Yvonne, M. W., Janssen et al., *Biology of disease—cell and tissue response to oxidation damage* 69:261–274 (1993).

Zubenko, G. et al., "Association of the apolipoprotein E epsilon 4 allele with clinical subtypes of autopsy-confirmed Alzheimer's disease", *American Journal of Medical Genetics*, 15;54(3):199–205.

We claim:

1. A method of inhibiting the vasoactive effects of β-amyloid peptides by exposing vessel to a modifier of superoxide formation prior to exposure of the vessel to a amyloid peptide.

2. A method according to claim 1 further including the step of modifying the vasoactive effect by exposing the vessel to a modifier of superoxide anion formation.

3. A method according to claim 2 further defined as exposing the vessel to a superoxide dismutase enzyme prior to said exposing step.

4. A method according to claim 1 further defined as exposing the vessel to a member of the group consisting essentially of β-amyloid antagonists, antioxidants, free radical scavengers and nitric acid donors.

5. A method of inhibiting vasoconstriction and neurodegeneration by antagonizing β-amyloid peptide induced vascular free radicals in excess of functional equilibrium by antagonizing vascular free radicals in excess of function equilibrium.

6. A method according to claim 5, wherein said antagonizing step is further defined as inactivating the free radical excess.

7. A method according to claim 5, wherein said antagonizing step is further defined as antagonists of superoxide anions consisting essentially of superoxide dismutase and compounds which enhance NO production.

8. A method to identify patients at risk for Alzheimer's Disease (AD), said method comprising the steps of:

1) measuring peripheral blood flow in a patient;
   2) administering a vasodilator;
   3) measuring peripheral blood flow in response to the vasodilator in the patient;
   4) identifying patients in which the vascular resistance is greater than in matched controls thereby distinguishing those at risk for Alzheimer's Disease (AD).

9. A method as set forth in claim 8 including the step of simultaneously monitoring oxygen contents in the blood.

* * * * *